US006821264B1

(12) United States Patent
Khurana et al.

(10) Patent No.: US 6,821,264 B1
(45) Date of Patent: Nov. 23, 2004

(54) GENE DELIVERY DEVICE AND GENE DELIVERY METHOD

(75) Inventors: Gautam Khurana, 2608 Tuxedo La. NW., Rochester, MN (US) 55901; Stephen James Russell, Rochester, MN (US); Zvonimir S. Katusic, Rochester, MN (US)

(73) Assignee: Gautam Khurana, Rochester, MN (US)

( * ) Notice: Subject to any disclaimer, the term of this patent is extended or adjusted under 35 U.S.C. 154(b) by 232 days.

(21) Appl. No.: 09/723,121

(22) Filed: Nov. 27, 2000

(51) Int. Cl.[7] ........................ A61M 37/00; A61M 31/00; C07H 21/04; A61K 31/70
(52) U.S. Cl. ........................ 604/46; 604/518; 604/522; 536/23.1; 514/44
(58) Field of Search ........................ 604/46, 518, 522; 514/44; 536/23.1

(56) References Cited

U.S. PATENT DOCUMENTS

| | | |
|---|---|---|
| 2,223,538 A | 12/1940 | Taylor et al. |
| 2,226,529 A | 12/1940 | Austin |
| 2,257,911 A | 10/1941 | Kraft |
| 2,372,669 A | 4/1945 | Haney |
| 2,418,482 A | 4/1947 | Robinsohn |
| 2,752,358 A | 6/1956 | Ehrhart |
| 2,874,153 A | 2/1959 | Bowman et al. |
| 2,882,263 A | 4/1959 | Natta et al. |
| 2,913,442 A | 11/1959 | Matlack |
| 2,916,475 A | 12/1959 | Caldwell et al. |
| 3,012,994 A | 12/1961 | Bell et al. |
| 3,112,300 A | 11/1963 | Natta et al. |
| 3,112,301 A | 11/1963 | Natta et al. |
| 3,143,527 A | 8/1964 | Wittbecker |
| 3,238,553 A | 3/1966 | Bailey et al. |
| 3,595,952 A | 7/1971 | Davidson et al. |
| 3,745,061 A | 7/1973 | Champaneria et al. |
| 4,279,053 A | 7/1981 | Payne et al. |
| 4,441,227 A | 4/1984 | d'Argembeau |
| 4,688,857 A | 8/1987 | Boucherie |
| 4,987,071 A | 1/1991 | Cech et al. |
| 5,274,873 A | 1/1994 | Shields |
| 5,318,514 A * | 6/1994 | Hofmann ............... 604/20 |
| 5,335,389 A | 8/1994 | Curtis et al. |
| 5,511,275 A | 4/1996 | Volpenhein et al. |
| 5,681,335 A | 10/1997 | Serra et al. |
| 6,004,806 A * | 12/1999 | McCall et al. ........... 435/325 |
| 6,127,525 A | 10/2000 | Crystal et al. |

FOREIGN PATENT DOCUMENTS

| | | | |
|---|---|---|---|
| WO | WO 95/15342 | | 6/1995 |
| WO | WO 99/08713 | * | 2/1999 |

OTHER PUBLICATIONS

Vicente, M et al. Inhibition of Plant Viruses by Human Gamma Interferon. Journal Phytopathol. 1987, vol. 119, No. 1 Abstract.*

Agrawal et al., "Oligodeoxynucleoside phosphoramidates and phosphorothioates as inhibitors of human immunodeficiency virus," *Proc. Natl. Acad. Sci. USA*, 1988, 85:7079–7083.

Barthel et al.,"Laboratory Methods—Gene Transfer Optimization with Lipospermine–Coated DNA," *DNA Cell Biology*,1993, 12(6):553–560.

Behr et al., "Efficient gene transfer into mammalian primary endocrine cells with lipopolyamine–coated DNA," *Proc. Natl. Acad. Sci. USA*, 1989, 86:6982–6986.

Bergelson et al., "Isolation of a Common Receptor for Coxsackie B Viruses and Adenoviruses 2 and 5," *Science*, 1997, 275:1320–1323.

Blau and Springer, "Molecular Medicine—Gene Therapy—A Novel Form of Drug Delivery," *New England J. Med.*, 1995, 333(18):1204–1207.

Boudin et al., "Isolation and Characterization of Adenovirus Type 2 Vertex Capsomer (Penton Base)," *Virology*, 1979, 92:125–138.

Brenner, "Reports of Adenovector "Death"Are Greatly Exaggerated," *Moi. Ther.*, 2000, 1(3):205.

Burch and Mahan, "Oligonucleotides Antisense to the Interleukin 1 Receptor mRNA Block the Effects of Interleukin 1 in Cultured Murine and Human Fibroblasts and in Mice," *J. Clin. Invest.*, 1991, 88:1190–1196.

Chapman et al.,"Gene Transfer Into Coronary Arteries of Intact Animals With a Percutaneous Balloon Catheter," *Circ. Res.*, 1992, 71:27–33.

Chen et al., "Multitarget–ribozyme directed to cleave at up to nine highly conserved HIV–1 env RNA regions inhibits HIV–1 replication–potential effectiveness against most presently sequenced HIV–1 isolates," *Nucleic Acids Res.*, 1992, 20(17):4581–4589.

Chen et al., "Expression and Funcation of Recombinant Endothelial Nitric Oxide Synthase Gene in Canine Basilar Artery," *Cir. Res.*, 1997, 80:327–335.

(List continued on next page.)

*Primary Examiner*—Anne-Marie Falk
*Assistant Examiner*—Celine Qian
(74) *Attorney, Agent, or Firm*—Fish & Richardson P.C., P.A.

(57) ABSTRACT

A gene delivery device for localizing and enhancing the efficacy of gene transfer that provides a contact surface for contacting with a tissue site. By applying a pharmaceutical composition comprising a nucleic acid to a contact surface and contacting the contact surface to a tissue site, a greater than 10-fold increase in transduction efficiency is achieved. In one embodiment of the invention, the device comprises a housing in communication with a contact surface having multiple contact elements, and the pharmaceutical composition is applied to the contact elements through a lumen in the device.

26 Claims, 14 Drawing Sheets

OTHER PUBLICATIONS

Chen et al., "Effects of in vivo adventitial expression of recombinant endothelial nitric oxide synthase gene in cerebral arteries," *Proc. Natl. Acad. Sci. USA*, 1997, 94:12568–12573.

Chen et al., "Transfer and expression of recombinant nitric oxide synthase genes in the cardiovascular system," *Trends in Pharmacological Sciences*, 1998, 19:276–286.

Clapp et al., "Fetal Liver Hematopoietic Stem Cells As a Target for in Utero Retroviral Gene Transfer," *Blood*, 1991, 78(4):1132–1139.

Collins and Olive, "Reaction Conditions and Kinetics of Self–Cleavage of a Ribozyme Derived from *Neurospora* VS RNA," *Biochem.*, 1993, 32:2795–2799.

Crawford–Miksza and Schnurr, "Analysis of 15 Adenovirus Hexon Proteins Reveals the Location and Structure of Seven Hypervariable Regions Containing Serotype–Specific Residues," *J. Virol.*, 1996, 70(3):1836–1844.

Crystal et al., "Administration of an adenovirus containing the human CFTR cDNA to the respiratory tract of individuals with cystic fibrosis," *Nat. Gen.*, 1994, 8:42–51.

Crystal, "Transfer of Genes to Humans: Early Lessons and Obstacles to Success," *Science*, 1995, 270:404–410.

Dropulić et al., "Functional Characterization of a U5 Ribozyme: Intracellular Suppression of Human Immunodeficiency Virus Type 1 Expression," *J. Virol.*, 1992, 66(3):1432–1441.

Dyer and Herrling, "Progress and Potential for Gene–Based Medicines," *Mol. Ther.*, 2000, 1(3):213–224.

Felgner et al., "Lipofection: A highly efficient, lipid–mediated DNA–transfection procedure," *Proc. Natl. Acad. Sci. USA*, 1987, 84:7413–7417.

Ferry et al., "Retroviral–mediated gene transfer into hepatocytes in vivo," *Proc. Natl. Acad. Sci. USA*, 1991, 88:8377–8381.

Guerrier–Takada et al., "The RNA Moiety of Ribonuclease P is the Catalytic Subunit of the Enzyme," *Cell*, 1983, 35:849–857.

Hampel and Tritz, "RNA Catalytic Properties of the Minimum (–)sTRSV Sequence," *Biochem.*, 1989, 28(12):4929–4933.

Hampel et al., "'Hairpin' Catalytic RNA model: evidence for helices and sequence requirement for substrate RNA," *Nucleic Acids Res.*, 1990, 18(2):299–304.

Heistad and Faraci, "Gene Therapy for Cerebral Vascular Disease," *Stroke*, 1996, 27(9):1688–1693.

Khurana et al., "Pathophysiological basis of cerebral vasospasm following aneurysmal subarachnoid haemorrhage," *J. Clin. Neuroscience*, 1997, 4(2):122–131.

Khurana et al., "Adenovirus–Mediated Gene Transfer to Human Cerebral Arteries," *J. Cereb. Blood Flow Metab.*, 2000, 20:1360–1371.

Kim et al., "Transcriptional Targeting of Replication–defective Adenovirus Transgene Expression to Smooth Muscle Cells in Vivo," *J. Clin. Invest.*, 1997, 100:1006–1014.

Kitsis et al., "Hormonal modulation of a gene injected into rat heart in vivo," *Proc. Natl. Acad. Sci. USA*, 1991, 88:4138–4142.

Leclerc et al., "Percutaneous Arterial Gene Transfer in a Rabbit Model," *J. Clin. Invest.*, 1992, 90:936–944.

Leonetti et al., "Antibody–targeted liposomes containing oligodeoxyribonucleotides complementary to viral RNA selectively inhibit viral replication," *Proc. Natl. Acad. Sci. USA*, 1990, 87:2448–2451.

Lim et al., "Direct in Vivo Gene Transfer Into the Coronary and Peripheral Vasculatures of the Intact Dog," *Circulation*, 1991, 83:2007–2011.

Loose–Mitchell, "Antisense nucleic acids as a potential class of pharmaceutical agents," *Trends in Pharmacological Science*, 1988, 9:45–47.

Marcus–Sekura, "Techniques for Using Antisense Oligodeoxyribonucleotides to Study Gene Expression," *Anal. Biochem.*, 1988, 172:289–295.

Morling and Russell, "Enhanced transduction efficiency of retroviral vectors coprecipitated with calcium phosphate," *Gene Therapy*, 1995, 2:504–508.

Nabel et al., "Recombinant Gene Expression in Vivo Within Endothelial Cells of the Arterial Wall," *Science*, 1989, 244:1342–1344.

Natta, "Une Nouvelle Classe de Polymeres d'α–Olefines ayant une Régularité de Structure Exceptionnelle," *J. Polymer Science*, 1955, 16:143–154 (Synopsis only is in English).

Newman et al., "Adenovirus–mediated Gene Transfer into Normal Rabbit Arteries Results in Prolonged Vascular Cell Activation, Inflammation, and Neointimal Hyperplasia," *J. Clin. Invest.*, 1995, 96:2955–2965.

O'Brien, "Gene transfer and vascular disease," *Journal of the irish Colleges of Physicians and Surgeons*, 1998, 27:33–39.

Ojwang et al., "Inhibition of human immunodeficiency virus type 1 expression by a hairpin ribozyme," *Proc. Nat., Acad. Sci. USA*, 1992, 89:10802–10806.

Onoue et al., "Adventitial Expression of Recombinant Endothelial Nitric Oxide Synthase Gene Reverses Vasoconstrictor Effect on Endothelin–1" *J. Cereb. Blood Flow Metab.*, 1999, 19(9):1029–1037.

Ooboshi et al., "Adenovirus–Mediated Gene Transfer in Vivo to Cerebral Blood Vessels and Perivascular Tissue," *Circ. Res.*, 1995, 77:7–13.

Perrotta and Been, "Cleavage of Olioribonucleotides by a Ribozyme Derived from the Hepatitis Virus RNA Sequence," *Biochem.*, 1992, 31:16–21.

Pettersson, "Structural and Nonstructural Adenovirus Proteins," *The Adenoviruses*, Ginsberg (ed.), 1984, Plenum Press, New York, NY, Chapter 6, pp. 205–270.

Price et al., "Lineage analysis in the vertebrate nervous system by retrovirus–mediated gene transfer," *Proc. Natl. Acad. Sci. USA*, 1987, 84:156–160.

Quantin et al., "Adenovirus as an expression vector in muscle cells in vivo," *Proc. Natl. Acad. Sci. USA*, 1992, 89:2581–2584.

Richter et al., "Adeno–associated virus vector transduction of vascular smooth muscle cells in vivo," *Physiol. Genomics*, 2000, 2:117–127.

Roberts et al., "Three–Dimensional Structure of the Adenovirus Major Coat Protein Hexon," *Science*, 1986, 232:1148–1151.

Rosenfeld et al., "Adenovirus–Mediated Transfer of a Recombinant α1–Antitrypsin Gene to the Lung Epithelium in Vivo," *Science*, 1991, 252:431–434.

Rosenfeld et al., "In Vivo Transfer of the Human Cystic Fibrosis Transmembrane Conductance Regulator Gene to the Airway Epithelium," *Cell*, 1992, 68:143–155.

Rossi et al., "Ribozymes as Anti–HIV–1 Therapeutic Agents: Principles, Applications, and Problems," *Aids Research and Human Retroviruses*, 1992, 8(2):183–189.

Sarin et al., "Inhibition of acquired immunodeficiency syndrome virus by oligodeoxynucleoside methylphosphonates," *Proc. Natl. Acad. Sci. USA*, 1988, 85:7448–7451.

Sarver et al., "Ribozymes as Potential Anti–HIV–1 Therapeutic Agenst," *Science*, 1990, 247:1222–1225.

Saville and Collins, "A Site–Specific Self–Cleavage Reaction Performed by a Novel RNA in Neurospora Mitochondria," *Cell*, 1990, 61:685–696.

Saville and Collins, "RNA–mediated ligation of self–cleavage products of a *Neurospora* mitochondrial plasmid transcript," *Proc. Natl. Acad. Sci. USA*, 1991, 88:8826–8830.

Scanlon et al., "Ribozyme–mediated cleavage of c–fos mRNA reduces gene expression of DNA synthesis enzymes and metallothionein," *Proc. Natl. Sci. USA*, 1991, 88:10591–10595.

Soriano et al., "Targeted and nontargeted liposomes for in vivo transfer to rat liver cells of a plasmid containing the preproinsulin I gene," *Proc. Natl. Acad. Sci. USA*, 1983, 80:7128–7131.

Spector and Samaniego, "Construction and Isolation of Recombinant Adenoviruses with Gene Replacements," *Methods in Molecular Genetics*, Adolph (ed.), 1995, Academic Press, Inc., San Diego, CA, vol. 7, pp. 31–44.

Stein and Cohen, "Oligodeoxynucleotides as Inhibitors of Gene Expression: A Review," *Cancer Res.*, 1988, 48:2659–2668.

Suzuki et al., "Heme oxygenase–1 gene induction as an intrinsic regulation against delayed cerebral vasospasm in rats," *J. Clin. Invest.*, 1999, 104:59–66.

Thierry and Dritschilo, "Intracellular availability of unmodified, phosphorothioated and liposomally encapsulated oligodeoxynucleotides for antisense activity," *Nucleic Acids Res.*, 1992, 20(21):5691–5698.

Thomas et al., "Peripheral infection with adenovirus causes unexpected long–term brain inflammation in animals injected intracranially with first–generation, but not with high–capacity, adenovirus vectors: Toward realistic long–term neurological gene therapy for chronic diseases," *Proc. Natl. Acad. Sci. USA*, 2000, 97(13):7482–7487.

Toyoda et al., "Gene transfer of calcitonin gene–related peptide to cerebral arteries," *Am. J. Physiol. Heart Circ. Physiol.*, 2000, 278:H586–H594.

Toyoda et al., "Calcium phosphate precipitates augment adenovirus–mediated gene transfer to blood vessels in vitro in vivo," *Gene Therapy*, 2000, 7:1284–1291.

Van der Krol et al., "Modulation of Eukaryotic Gene Expression by Complementary RNA or DNA Sequence," *BioTechniques*, 1988, 6(10):958–975.

Vassalli et al., "A Mouse Model of Arterial Gene Transfer Antigen–Specific Immunity Is a Minor Determinant of the Early Loss of Adenovirus–Mediated Transgene Expression," *Cir. Res.*, 1999, 85:e25–e32.

Von der Leyen et al., "Gene therapy inhibiting neointimal vascular lesion: In vivo transfer of endothelial cell nitric oxide synthase gene," *Proc. Natl. Acad. Sci. USA*, 1995, 92:1137–1141.

Walder, "Antisense DNA and RNA: progress and prospects," *Genes & Development*, 1988, 2:502–504.

Wang and Huang, "pH–sensitive immunoliposomes mediate target–cell–specific delivery and controlled expression of a foreign gene in mouse," *Proc. Natl. Acad. Sci. USA*, 1987, 84:7851–7855.

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *J. Virol.*, 1991 65(10):5531–5534.

Wen et al., "Second–Generation Adenoviral Vectors Do Not Prevent Rapid Loss of Transgene Expression and Vector DNA From the Arterial Wall," *Arterioscler. Thromb. Vasc. Biol.*, 2000, 20:1452–1458.

Wickham et al., "Integrins $\alpha_v\beta_3$ $\alpha_v\beta_5$ Promote Adenovirus Internalization but Not Virus Attachment," *Cell*, 73:309–319.

Wolff et al., "Direct Gene Transfer into Mouse Muscle in Vivo," *Science*, 1990, 247:1465–1468.

Wood et al., "Immune responses to adenovirus vectors in the nervous system," *Trends in Neurosciences*, 1996, 19(11):497–500.

Woolf et al., "Specificity of antisense oligonucleotides in vivo," *Proc. Natl. Acad. Sci. USA*, 1992, 89:7305–7309.

Yei et al., "Adenovirus–mediated gene transfer for cystic fribrosis: quantitative evalution of repeated in vivo vector administration to the lung," *Gene Therapy*, 1994, 1(3):192–200.

Zhu et al., "Systemic Gene Expression After Intravenous DNA Delivery into Adult Mice," *Science*, 1993, 261:209–211.

Zon, "Synthesis of Backbone–Modified DNA Analogues for Biological Applications," *J. Protein Chem.*, 1987, 6(2):131–145.

Zon, "Oligonucleotide Analogues as Potential Chemotherapeutic Agents," *Pharmaceutical Res.*, 1988, 5(9):539–549.

* cited by examiner

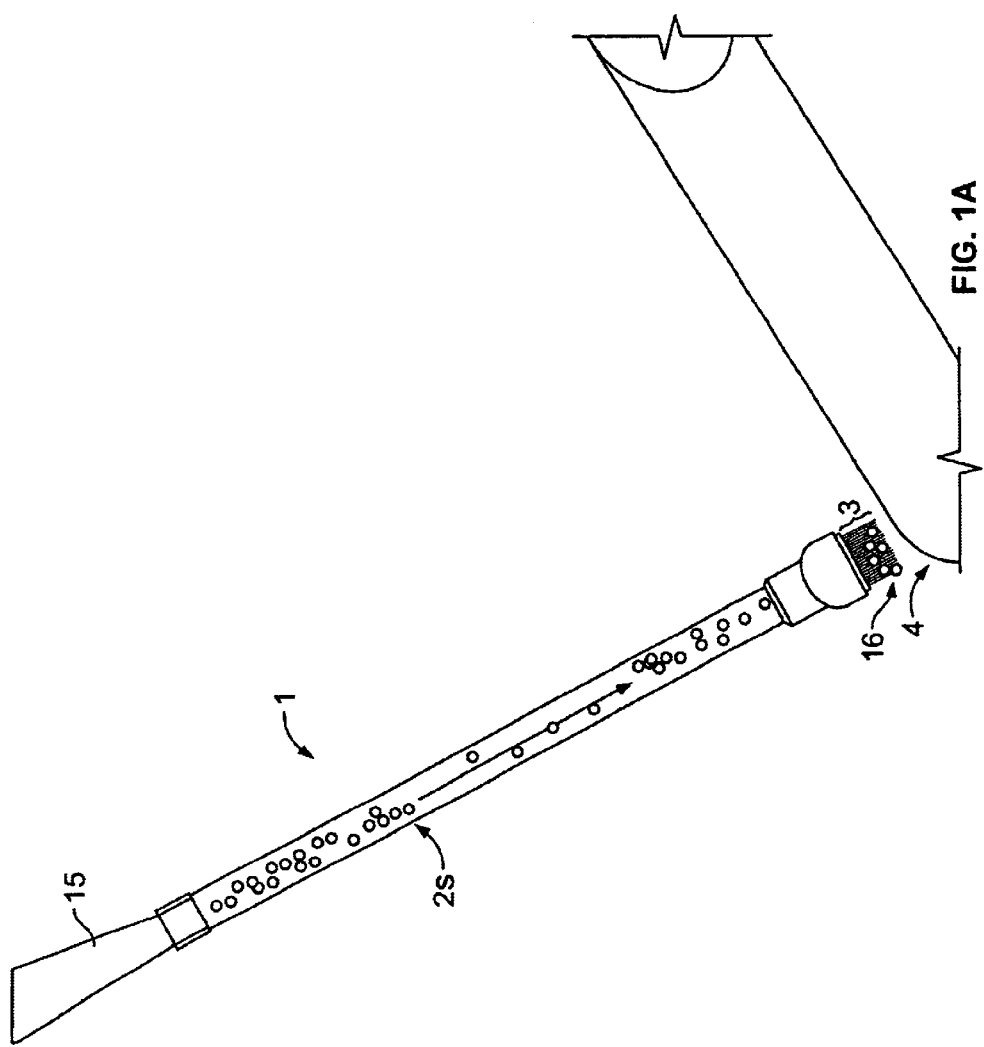

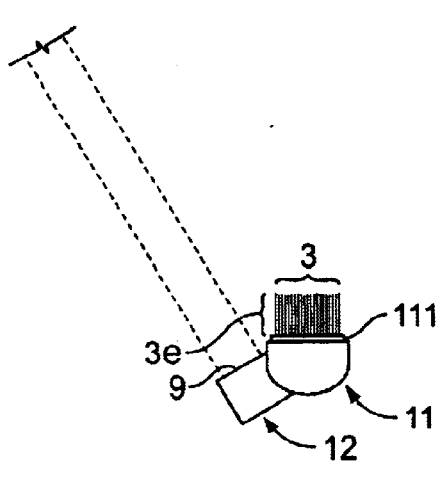
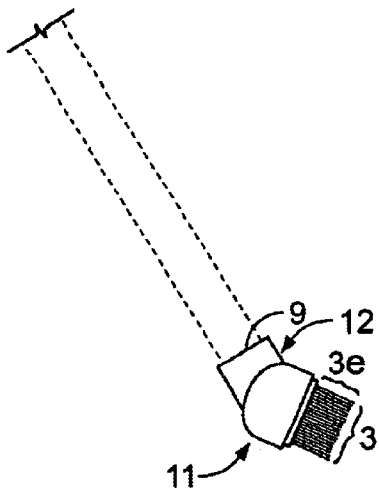
FIG. 3D  FIG. 3E
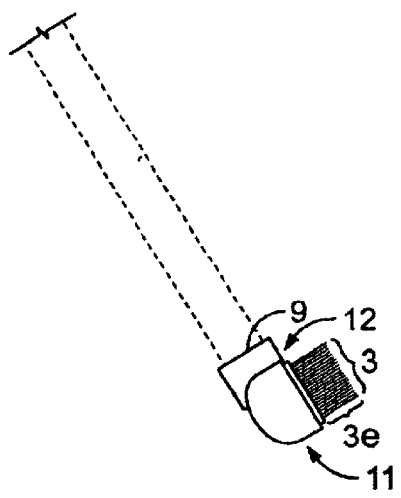
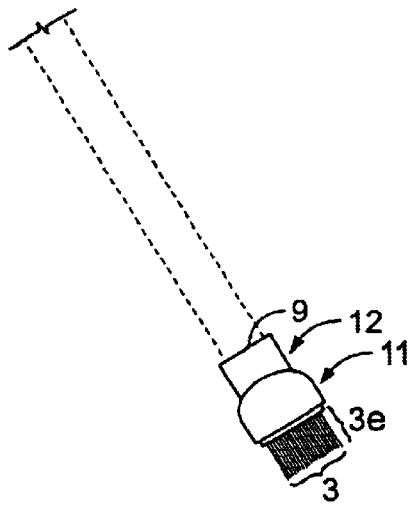
FIG. 3F  FIG. 3G

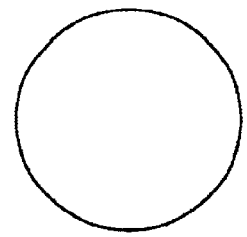
FIG. 4B
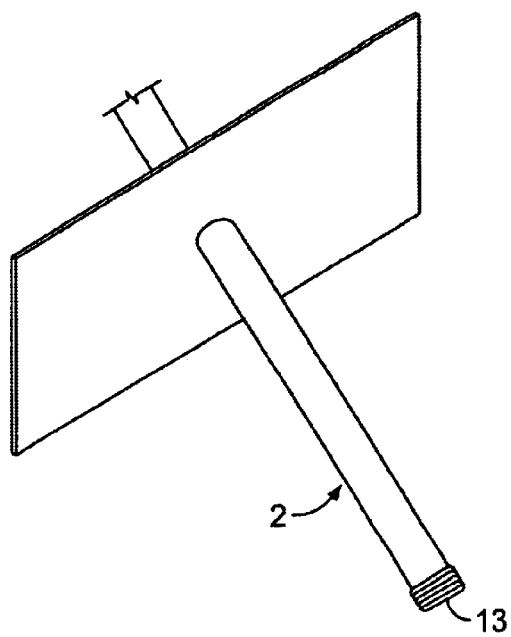
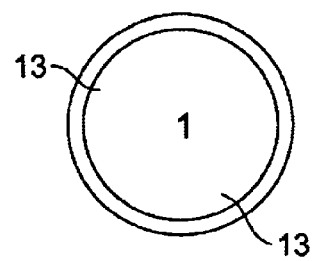
FIG. 4C
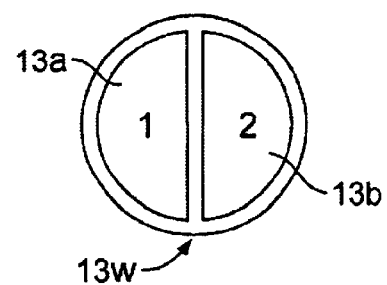
FIG. 4A
FIG. 4D

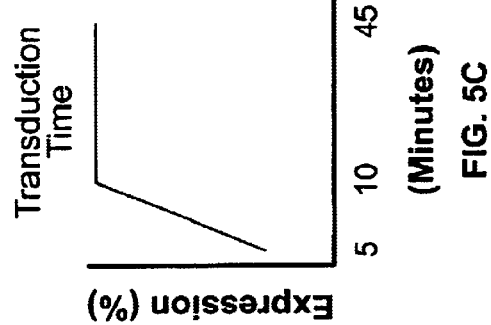
FIG. 5C
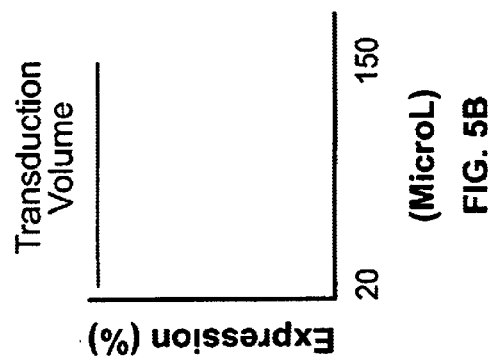
FIG. 5B
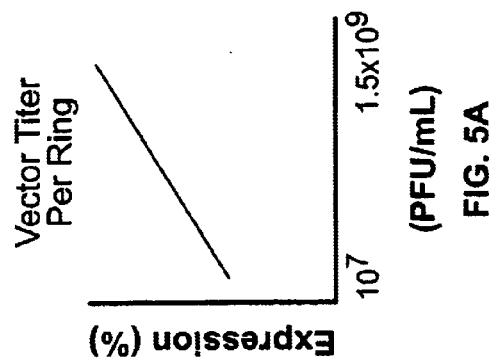
FIG. 5A
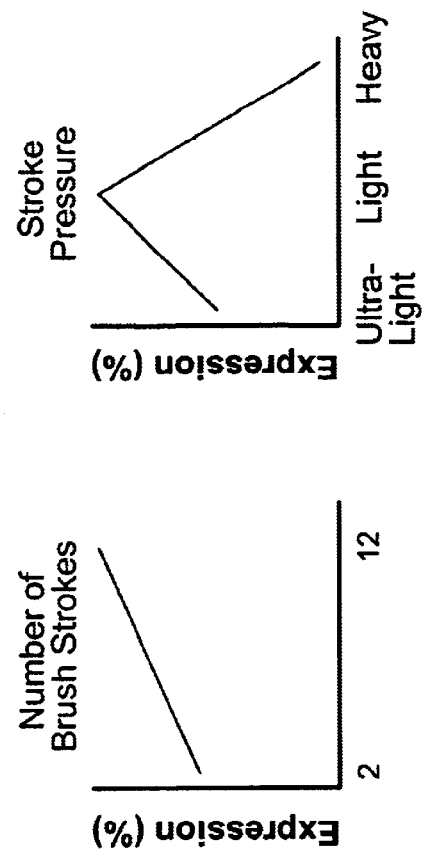
FIG. 5F
FIG. 5E
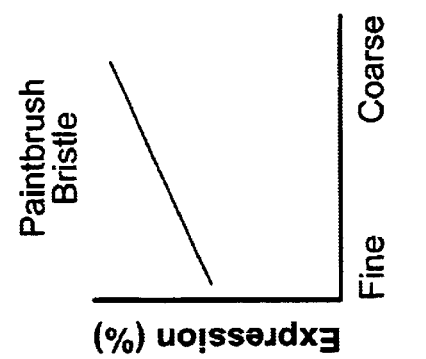
FIG. 5D ZFGB (Side View)

NCB=Negative Control Brushed
ZD=LacZ Drops/Immersion Method
ZB=LacZ Brushed without FG
ZFGB=LacZ Brushed with FG Present
Titer=10$^9$ PFU/Ring

NCB    ZD    ZB    ZFGB

GENE DELIVERY DEVICE AND GENE DELIVERY METHOD

FIELD OF THE INVENTION

The invention relates to a gene delivery device for localizing and enhancing the efficacy of gene transfer.

BACKGROUND OF THE INVENTION

Gene transfer is a powerful technique which uses a biological vehicle (such as an engineered adenovirus) to introduce a specific gene of interest into a target tissue. Studies have characterized the morphologic, biochemical, and functional effects of recombinant gene expression in a wide variety of tissues, including animal and human cerebral arteries, and support the applicability of gene therapy for the treatment of vascular diseases, including cerebrovascular disease (Chen, et al., Trends in Pharmacological Sciences 19: 276–286,1998; Khurana, et al., Journal of Cerebral Blood Flow and Metabolism 20: 1360–1371,2000).

Ooboshi, et al. (Circulation Research 77: 7–13,1995) carried out the first gene transfer to cerebral arteries in vivo. In their purely morphologic study, the investigators delivered a replication-incompetent adenoviral vector (expressing recombinant β-galactosidase gene) into the cerebrospinal fluid (CSF) of Sprague-Dawley rats held in various anatomical positions. One to seven days following injection, the transduced brains of the animals were examined histochemically after appropriate staining. The authors reported: 1. Distribution of recombinant protein staining consistent with the anatomical position in which the rat was held; 2. Good transduction of the adventitial layer of large and small cerebral arteries (consistent with perivascular gene delivery); and 3. Undetectable β-galactosidase expression by day seven following injection (i.e., indicative of short-term recombinant gene expression). In the first functional study of transduced intracranial arteries, Chen, et al. (Circulation Research 80: 327–25 335,1997) reported the morphologic, biochemical, and vasomotor effects of ex vivo transduction of canine basilar artery with an adenoviral (Ad) vector expressing recombinant endothelial nitric oxide synthase (eNOS). Their principal findings were: 1. Recombinant protein was expressed mainly in the adventitia and, to a lesser extent, in the endothelium of transduced arteries (consistent with ex vivo transduction); 2. Expression of recombinant eNOS in the arterial wall was associated with beneficial vasomotor effects including significantly enhanced relaxations to calcium ionophore A23187, a compound whose receptor-independent relaxing actions are nitric oxide (NO)-mediated, and reduced contractions to uridine triphosphate; and 3. Basal production of cyclic 3'5'-guanosine monophosphate (cGMP; the second messenger for NO-mediated signaling) was significantly increased in AdeNOS-transduced arteries. Immediately following this study, similar findings were reported by Chen, et al. (Proceedings of the National Academy of Sciences of the United States of America (PNAS) 94: 12568–12573,1997) in vivo in dogs. Together, these studies indicated that cerebral arterial tone could be favorably modulated by recombinant eNOS expression in the vessel wall, i.e., that gene transfer could achieve a therapeutic effect. That these findings are reproducible in nonpostmortem human cerebral arteries has been recently demonstrated by Khurana, et al. (supra).

To date, most ex vivo and in vivo gene transfer studies in the cardiovascular system have utilized recombinant adenoviruses in the titer range of $10^9$–$10^{10}$ plaque forming units (PFU), exposing tissues to approximately 1 to 10 billion infectious (viral) units. Based on studies related to cerebrovascular gene transfer, this translates to exposing each target cell to approximately 1000 infectious units, thereby setting the stage for excessive immunogenicity and cytotoxicity from the relatively large "vector load." Despite the large amounts of virus being delivered to tissue sites, experiments involving recombinant β-galactosidase- or luciferase-based quantification of adenovirus-mediated gene transfer efficiency demonstrate relatively poor transduction of arteries ex vivo, which is likely to be even poorer in vivo (Heistad, et al., Stroke 27: 1688–1693,1996). To some extent this phenomenon may be attributable to a relative paucity of coxsackie virus-adenovirus receptor (CAR), in cerebral arteries (Heistad, et al., supra). However, regardless of the underlying reason(s), development of techniques to greatly reduce the number of infectious units delivered to tissues, including blood vessels, ex vivo and ultimately in vivo, is required in order to reduce the likelihood and severity of an adverse response to the vector due to the sheer number of particles delivered to the host.

Several recent publications have reported the feasibility of direct gene transfer, without the use of viral vectors, into tissues such as muscle (Ferry, et al., PNAS 88: 8777–8781, 1991; Quantin, et al., PNAS 89: 2581–2584,1992), hematopoletic stem cells (Clapp, et al., Blood 78: 1132–1139,1991), arterial wall (Nabel, et al., Science 2: 1342–1344,1989), nerve (Price, et al., PNAS 84: 156–160,1987), and lung (Rosenfeld, et al., Science 252: 431–434,1991). Direct injection of DNA into skeletal muscle, (Wolff, et al., Science 247: 1465–1468,1990) and heart (Kitsis, et al., PNAS 88: 4138–4142,1991), and injection of DNA-lipid complexes into the vasculature (Lim, et al., Circulation 83: 2007–2011, 1991; Leclerc, et al., Journal of Clinical Investigation 90: 936–944,1992; Chapman, et al., Circulation Research 71: 27–33,1992) has also been reported to yield a detectable level of recombinant gene-product expression in vivo. However, conventional vector delivery methods, including ex vivo "dripping" or "immersion techniques, and in vivo dripping or injection, remain inefficient and poorly tissue-specific.

Heistad and colleagues (supra) first reported the use of a mechanical method, namely controlled animal head-tilt, to assist in localizing vectors injected into the CSF via the cisterna magna to arteries in the circle of Willis. While this technique is helpful, it remains relatively nonspecific and operator-dependent. A molecular targeting technique using a cell-specific promoter such as SM22α (selective for smooth muscle cells) rather than a cell-nonspecific promoter such as that derived from cytomegalovirus (CMV) has been demonstrated to be effective in vitro (Kim, et al., Journal of Clinical Investigation 100: 1006–1014,1997), and may be useful in vivo to selectively target vascular as opposed to neuronal or glial tissue. However, at present, there is no way to reliably distinguish between smooth muscle cells in different cerebral arteries, and therefore the problem of being able to target specific vascular territories remains unsolved using this approach.

SUMMARY OF THE INVENTION

The invention provides a device and method for increasing the efficiency of gene transfer by localizing a vector at a desired tissue site and by increasing the uptake of the vector by cells at the tissue site. In one embodiment, the invention provides a method for delivering a pharmaceutical composition comprising a nucleic acid to a tissue site. The method comprises the steps of providing a gene delivery device comprising a contact surface, and applying the pharmaceutical composition to the contact surface. The contact surface is then contacted to the tissue, thereby placing and localizing the pharmaceutical composition at the tissue site. Contact with the tissue by the contact surface significantly enhances transduction of the tissue by the nucleic acid relative to transduction of noncontacted tissue to which the pharmaceutical composition is applied. In one embodiment of the invention, transduction efficiency is enhanced greater than 10-fold.

In one embodiment of the invention, the pharmaceutical composition comprises a nucleic acid selected from the group consisting of DNA, RNA, anti-sense molecules, triple-helix-forming nucleic acids, aptamers, and ribozymes. In another embodiment of the invention, the nucleic acid is encapsulated, such as by viral proteins or by a liposome coat. In a further embodiment of the invention, the nucleic acid is an adenoviral vector encapsulated by adenoviral glycoproteins, and transduction of cells at the tissue site includes infection by the adenovirus. In still a further embodiment of the invention, the nucleic acid is bound to or associated with a targeting molecule which binds to a cell at the tissue site.

In one embodiment of the invention, the pharmaceutical composition is placed at the tissue site along with a polymer compound which coats the tissue site. In one embodiment of the invention, the polymer compound is a tissue glue (e.g., fibrin glue); in another embodiment of the invention, the polymer compound is a hydrogel.

In one embodiment of the invention, the contacting is performed by moving the contact surface across the tissue site, such as by a back and forth and/or circular motion. In one embodiment, the contacting compresses tissue at the tissue site relative to noncontacted tissue, while in another embodiment, the contacting causes a portion of the tissue site to temporarily lie over another portion of the tissue site. In still another embodiment of the invention, cells at the tissue site are abraded in the process of contacting.

In one embodiment of the invention, tissue sites include, but are not limited to, the outer or inner surface of a blood vessel, skin, wounded tissue, mucosa, the outer or inner surface of an abdominal or thoracic or special sensory organ, the cortical or ventricular surface or parenchyma of the brain, the spinal cord or its surrounding tissue, meningeal tissue, a muscle, tendon, cartilage, joint, or bone. In one embodiment, the tissue site is cerebrovascular tissue. In another embodiment, the tissue site is cardiovascular tissue.

In one embodiment of the invention, the tissue site is contacted with the contact surface through an open surgical field. In another embodiment of the invention, the contact surface is first inserted into the lumen of an organ or a vessel prior to contacting a tissue site, such as by using a medical access device, such as a catheter or endoscope. In one embodiment of the invention, the contact surface is part of a gene delivery device, at least a portion of which is radiopaque.

In still another embodiment of the invention, the pharmaceutical composition comprises a solution which comprises detectable moieties, and placement and localization of the pharmaceutical composition at the tissue site is monitored by detecting the detectable moieties. In one embodiment of the invention, the solution comprises green-fluorescent protein (GFP). In another embodiment of the invention, the solution itself is radiopaque. In yet another embodiment of the invention, the solution contains a dye visualizable by the naked eye.

In still a further embodiment of the invention, the contact surface is in communication with an optical system including a light source, a light-transmitting element, one end of which is in proximity to the contact surface, and a detector. In this embodiment, contacting of the contact surface with the tissue site is monitored by detecting light transmitted from the light source through the transmitting element. In the embodiment of the invention where the pharmaceutical composition comprises a solution which comprises detectable moieties, placement and localization of the pharmaceutical composition can also be monitored. In one embodiment of the invention, the compression or folding of tissue is monitored. In still another embodiment, the placing and/or uptake of the pharmaceutical composition is monitored. In a further embodiment of the invention, the monitoring of the compression or folding of tissue and/or of the placing and/or uptake of the pharmaceutical composition is used to determine whether further contacting is necessary. In still a further embodiment, the medical access device comprises a cutting element, and a tissue site is exposed to the contact surface by the cutting element, prior to contacting with the contact surface. In one embodiment, the cutting element is a laser.

In one embodiment of the invention, the contact surface comprises a plurality of contact elements, such as bristles, fibers, the protrusions of a sponge, prongs, tines, and the like. In another embodiment of the invention, the contact elements are the bristles of a paintbrush. In one embodiment of the invention, a gene delivery device comprising a contact surface is used to contact the tissue and to deliver the pharmaceutical composition. In still another embodiment of the invention, the contact surface is a surgeon's gloved finger.

In one embodiment of the invention, the gene delivery device comprises a lumen with an opening in proximity to the contact surface, and the pharmaceutical composition is delivered to the contact surface through the lumen. In another embodiment of the invention, the pharmaceutical composition further comprises a polymerizable compound which polymerizes when the contact surface is contacted to the tissue site. In still another embodiment of the invention, the lumen is divided into a first and second channel sharing a common wall and the pharmaceutical composition and polymerizable compound are delivered through the first channel while a polymerizing agent is delivered through the second channel. When the polymerizable composition and pharmaceutical composition and polymerizing agent come into contact with each other at the tissue site, the polymerizable composition polymerizes, further localizing the pharmaceutical composition at the tissue site.

In one embodiment of the invention, a gene delivery device for use in performing the method is provided which comprises a shaft coupled to a contact surface. In one embodiment, the shaft comprises a shaft housing having a first end and a second end and defining a lumen. The first end comprises an opening and is in communication with a contact surface for contacting a tissue. However, in another embodiment, the first end comprises a plurality of openings.

In one embodiment of the invention, the contact surface comprises a plurality of elongated contact elements, each contact element comprising a base and a distal tip, the base being joined to the first end of the shaft housing and the distal tips separate from each other. In one embodiment, each contact element is a bristle, a fiber, tine, or a prong. In one embodiment of the invention, the plurality of contact elements at least partially surround the opening. In a further embodiment, the contact elements comprise a longitudinal axis which is at a less than 180 degree angle with respect to the longitudinal axis of the shaft housing.

In one embodiment of the invention, the contact surface is a porous material, such as a sponge, which is fixed to the first end of the shaft housing. In another embodiment, the porous material comprises a plurality of protrusions or contact elements, for contacting a tissue site. In still another embodiment, the contact surface comprises a funnel-shaped extension of the first end and the opening comprises the base of the funnel. In a further embodiment of the invention, the funnel-shaped extension comprises a spongiform material. In still a further embodiment of the invention, the first end is detachable from said shaft housing, and one type of first end can be exchanged for another. In another embodiment, attachments are provided for connection with the opening of the first end. For example, in one embodiment, a beveled needle is attached to the opening.

In one embodiment, the second end of the shaft housing is connectable to a syringe, through which the pharmaceutical composition can be delivered to the lumen of the shaft housing. In one embodiment, the syringe is a double-barreled syringe. In still a further embodiment of the invention, delivery of the composition through the syringe is controlled by a motorized element which creates positive or negative pressure within the body of the syringe. In this embodiment, the motorized element can be controlled by a motion of the hand or foot of the operator (e.g., such as by a foot pedal in communication with the motorized element). In still a further embodiment of the invention, the dosage of the pharmaceutical composition is controlled by a processor in communication with an optical system being used to monitor the movement of the contact surface and/or the placement and/or uptake of the pharmaceutical composition.

In another embodiment, kits are provided to facilitate performing the method. In one embodiment, the kit comprises a gene delivery device comprising a contact surface for contacting a tissue; and a pharmaceutical composition comprising a detectable moiety or nucleic acid, or both. In another embodiment of the invention, the gene delivery device comprises a graspable surface for attachment to a contact surface, at least one contact surface for attachment to the graspable surface, and a pharmaceutical composition. In one embodiment of the invention, the gene delivery device is a brush, such as a paintbrush or a toothbrush, or a brush with radially projecting bristles or fibers.

In one embodiment of the invention, the nucleic acids within the pharmaceutical composition are selected from the group consisting of DNA, RNA, anti-sense molecules, triple-helix-forming nucleic acids, aptamers, and ribozymes. In another embodiment of the invention, the nucleic acid is a viral vector, such as an adenoviral vector. In still another embodiment of the invention, the kit includes helper cells or molecules for amplifying the adenoviral vector and for providing a renewable source of the pharmaceutical composition.

In one embodiment of the invention, the gene delivery device is coated with an agent which minimizes adhesion of the pharmaceutical composition to the contact surface and/or the gene delivery device. The use of the anti-adhesive agent is optimized depending on the type of nucleic acid present in the pharmaceutical composition. For example, when the pharmaceutical composition comprises naked DNA, the agent is a DNA repellant such as silane. In an embodiment of the invention where the nucleic acid is encapsulated with viral glycoproteins, the agent is a charged molecule, such as polylysine.

In a further embodiment of the invention, the kit includes a polymerizable compound and a polymerizing agent for enhancing localization of the nucleic acid at the tissue site. In another embodiment of the invention, the polymerizable compound is fibrinogen and the polymerizing agent is thrombin. In a further embodiment of the invention, the pharmaceutical composition comprises detectable moieties, while in a further embodiment of the invention, the kit comprises a solution of detectable moieties which can be added to the pharmaceutical composition.

In one embodiment of the invention, the gene delivery device within the kit comprises a graspable surface having a longitudinal axis and the contact surface is detachable from the graspable surface. In another embodiment, the kit comprises a plurality of contact surfaces, each of which are differently angulated with respect to the longitudinal axis of the grasping element. In still another embodiment, the gene delivery device comprises a shaft housing defining a lumen and having an opening in proximity with the contact surface, the lumen for delivering the pharmaceutical composition to a tissue site being contacted by the contact surface. In a farther embodiment, the contact surface is detachable from the housing. In still a further embodiment, the device comprises a lumen which is turn comprises a first and second channel. The first and second channel can share a common wall. In one embodiment of the invention, the kit comprises a selection of different housings. In another embodiment of the invention, the kit comprises selections of different housings, syringes, adapters, and conduit-tubing for attachment to the gene delivery device.

The use of the device according to the present invention can also be facilitated by providing instructions with the kit. In one embodiment of the invention, the kit comprises instructions including data such as to how to perform the steps of the method. In another embodiment of the invention, the instructions are provided on a CD-ROM or video, or the like.

BRIEF DESCRIPTION OF THE INVENTION

The objects and features of the invention can be better understood with reference to the following detailed description and accompanying drawings. In general, the same elements within the figures are labeled with the same reference numbers. The figures are not to scale.

FIGS. 1A and 1B shows a gene delivery device according to one embodiment of the invention. FIG. 1A shows a device comprising a shaft housing defining a lumen and having a first end in communication with a contact surface, and a second end which is connectable to a syringe or conduit-tubing or other delivery device. The contact surface comprises a plurality of contact elements, or bristles. A pharmaceutical composition comprising nucleic acids (represented by circles in the Figure) is delivered through the lumen and brushed onto a target tissue surface. FIG. 1B shows contacting of the target tissue surface with the pharmaceutical composition using the contact surface.

FIGS. 2A and 2B shows a gene delivery device comprising detachable sections, according to one embodiment of the invention. FIG. 2A shows a device comprising a shaft housing defining a lumen, a first adapter section, connectable to a first end comprising a contact section, and a second adapter section, connectable to a syringe or conduit-tubing or other delivery device. FIG. 2B shows a shaft housing detached from its contact section.

FIGS. 3A–I show a gene delivery device comprising detachable sections, and different contact sections for attachment to the first adapter section. FIG. 3A shows a shaft housing detached from its contact section. FIG. 3B shows a contact section whose contact surface comprises a plurality of bristles. FIG. 3C shows a contact section comprising a spongiform material. FIGS. 3D–G show contact sections comprising contact surfaces which are articulable relative to the longitudinal axis of the shaft housing. FIG. 3H shows a funnel-shaped contact surface according to one embodiment of the invention. FIG. 3I, shows the contact surface of FIG. 3H comprising a protruding beveled needle.

FIGS. 4A–D show different shaft housing configurations for the gene delivery device according to one embodiment of the invention. FIG. 4A shows a housing through which a transverse section is taken and illustrated in FIGS. 4B–D. FIG. 4B shows a transverse section of a housing according to one embodiment of the invention, where the housing is solid throughout. FIG. 4C shows a transverse section of a housing according to another embodiment of the invention, where the housing defines a lumen. FIG. 4D shows a transverse section of a housing according to a further embodiment of the invention where the housing defines a lumen which is divided into a first and second channel sharing a common wall.

FIGS. 5A–F show the effect of different parameters on gene delivery using devices according to embodiments on the invention. The efficacy of gene transfer is measured by percent (%) expression of a recombinant gene in cells at a tissue site contacted by the contact surface of the device. FIG. 5A shows the effect of viral titer on % expression. FIG. 5B shows the effect of the volume of the pharmaceutical composition transduced. FIG. 5C shows the effect of transduction time. FIG. 5D shows the effect of different types of contact elements. FIG. 5E shows the effect of the number of strokes of the contact elements, when the contact elements are the bristles of a brush. FIG. 5F shows the effect of stroke pressure when the contact elements are the bristles of a brush.

FIGS. 6A–E show the effect of using a gene delivery device according to one embodiment of the invention, on expression of a marker gene encoding β-galactosidase.

Figure 9:
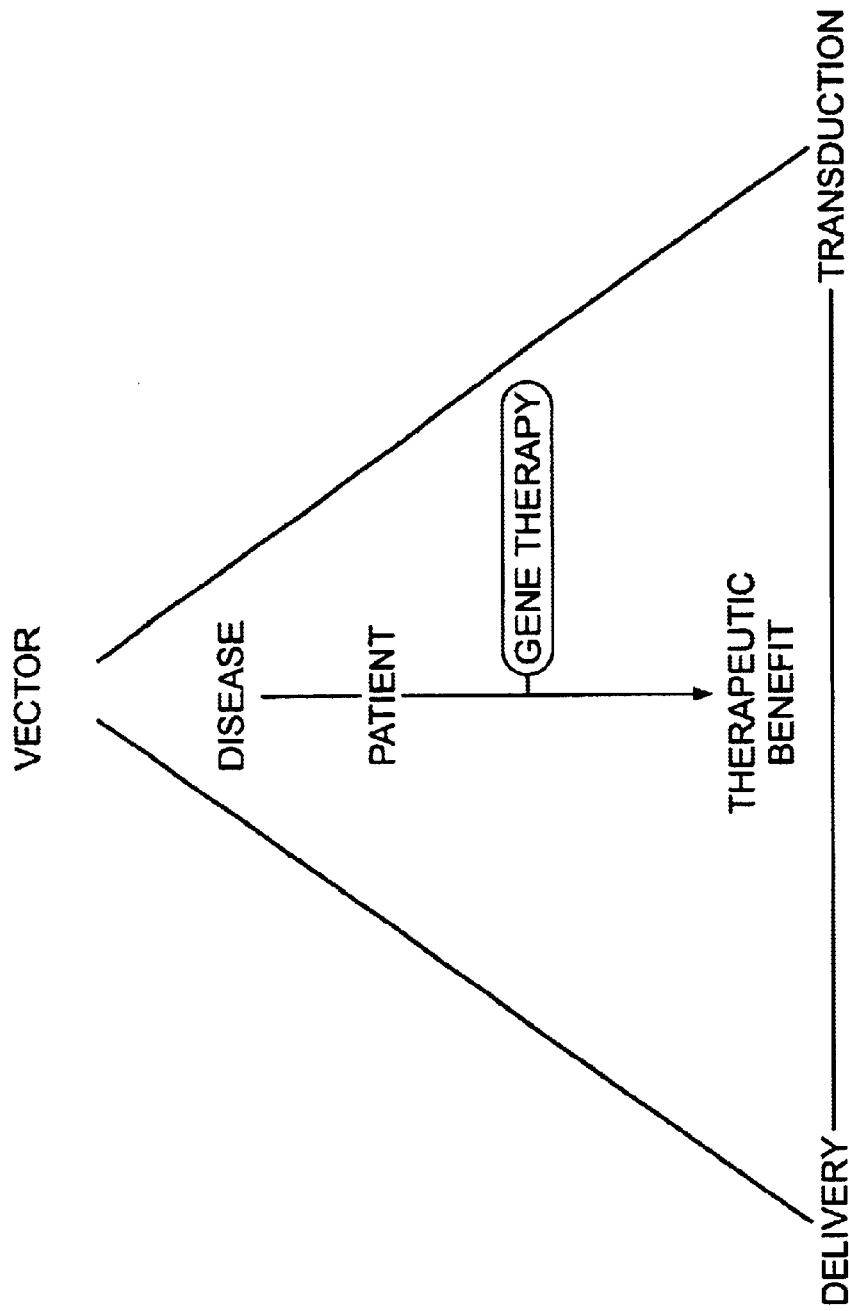

FIG. 9 schematically shows the clinical paradigm of gene therapy, and the three key areas of this technology (i.e., vector, delivery, and transduction).

DETAILED DESCRIPTION

The invention provides a gene delivery device for enhancing the localization and uptake of nucleic acids at a tissue site. The gene delivery device can be used to provide a variety of different types of nucleic acids to confer a missing or altered function on a cell. In one embodiment of the invention, a method is provided for selectively and efficiently transducing target cells at a tissue site. In another embodiment of the invention, kits are provided to facilitate using the device and performing the method.

Definitions

In order to more clearly and concisely describe and point out the subject matter of the claimed invention, the following definitions are provided for specific terms which are used in the following written description and the appended claims:

As defined herein, a "therapeutic gene" is a gene that corrects or compensates for an underlying molecular deficit or, alternatively, is a gene that is capable of up- or down-regulating a particular gene, or counteracting the negative effects of its encoded product, in a given disease state or syndrome.

As defined herein, "fine bristle" refers to non-stiff, non-abrasive hair-like fibers, while "coarse bristle" refers to stiff, hair-like fibers which can be abrasive. An example of a fine-bristle brush is one whose contact elements are comprised of camel hair. An example of a course-bristle brush is one whose contact elements are comprised of pig or horse hair, or a stiff synthetic fiber.

As defined herein, "stroke pressure" is defined qualitatively as "ultralight," "light" or "heavy." Ultralight pressure is that which results in no deformation of an arterial ring contacted with the gene delivery device. Light pressure is pressure that results in 15% or less of a change in the diameter of the ring upon contact. Heavy pressure results in greater than 15% deformation of the ring. Heaviest pressure results in complete flattening of the ring (100% deformation), with total closure or occlusion of the lumen.

As defined herein, a "tissue site" is a portion of tissue which the user contacts with the contact surface of the gene delivery device.

As defined herein, a "medical access device" is a device through which, or with assistance of which, the gene delivery device can be inserted and positioned at a target site within a body space such as the outer surface of a viscus (a body organ) or vessel, or the lumen of a hollow organ or blood vessel.

Gene Delivery Device

Figure 1B:
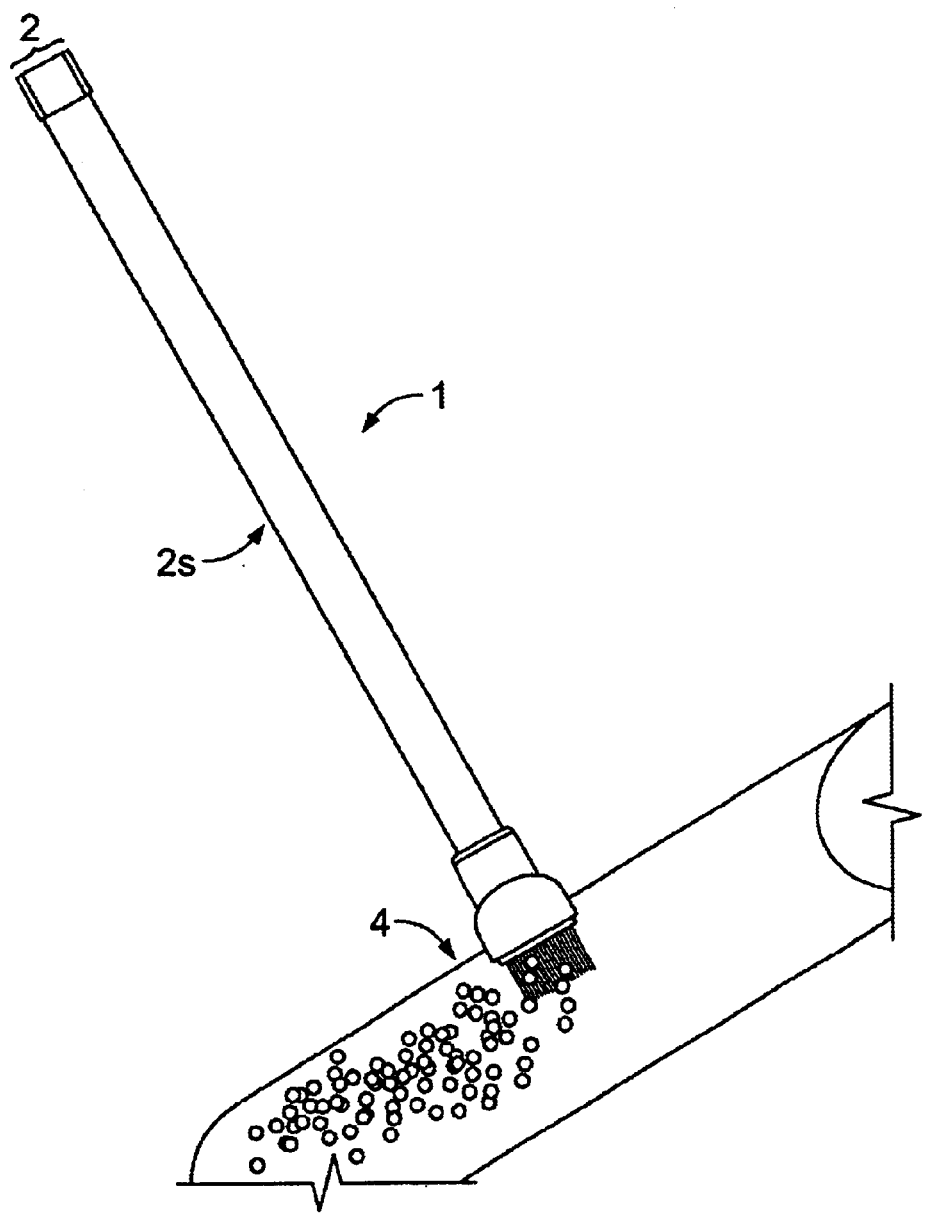

In one embodiment of the invention, as shown in FIGS. 1A and 1B, a gene delivery device 1 comprises a contact surface 3 coupled to a shaft 3 for contacting a tissue site 4. In one embodiment, the contact surface 3 and the shaft 3 cannot be separated from each other. However, in another embodiment of the invention, as shown in FIGS. 2A and 2B, the device 1 comprises a contact surface 3 which is detachable from the shaft 2, so that a plurality of different kinds of shafts 2 can be used with a plurality of different contact surfaces 3.

The Contact Surface

Figure 2A:
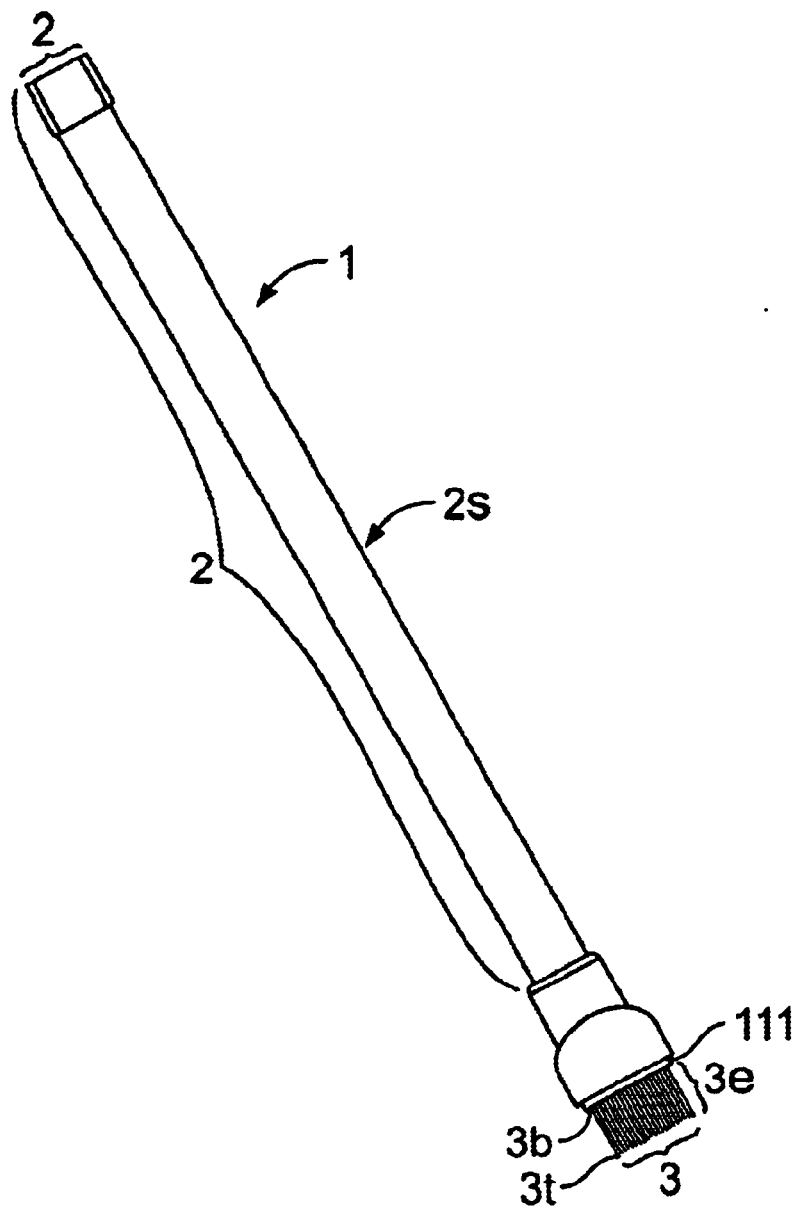
Figure 2B:
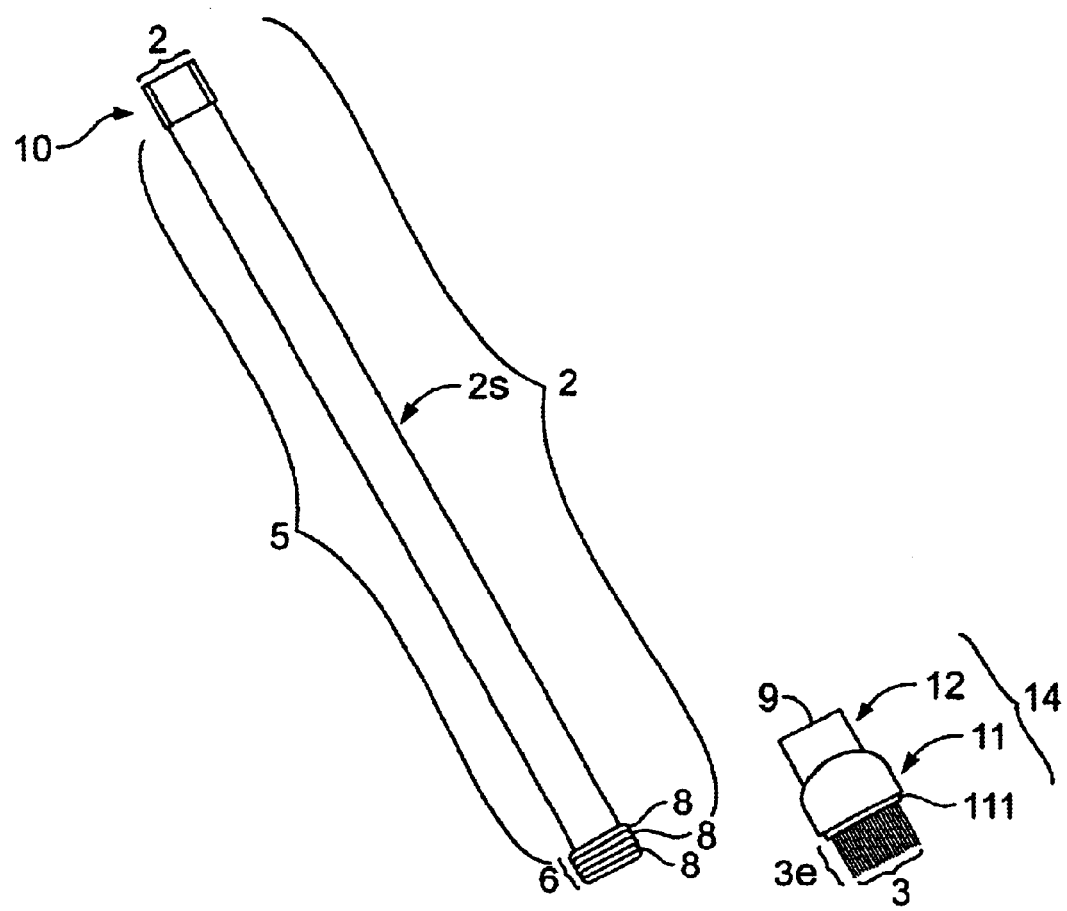

In one embodiment of the invention as shown in FIGS. 2A and 2B, the contact surface is part of a contact section 14 of the device which comprises a head 11 and a plurality of elongated contact elements 3e, each contact element 3e comprising a base 3b and a distal tip 3t, the base 3b of each contact element 3e being joined to a first end 111 of the head 1. The head is attached to a neck 12 which comprises a connection end 9 for connecting to the shaft 2. In one embodiment of the invention, each base of each contact element is joined to the first end 111 of the head 11 by a biocompatible, medical-grade adhesive, such as an epoxy or a silicone adhesive, or a commercially available adhesive such as TRA-CON TRA-BOND FDA-2 (Tra-Con Inc., Medford, Mass.). In one embodiment of the invention, the head 11 is separable from the neck 12 and can be replaced with another head 11 as desired or indicated (e.g., to facilitate access to a tissue site, or when the contact elements 3e of the contact surface 3 become worn). In one embodiment of the invention, an opening in the first end 111 of the head 11 communicates with a lumen 13 in the shaft 2, enabling a pharmaceutical composition within the lumen to come into contact with the contact elements 3e. In one embodiment of the invention, the contact elements 3e are disposed radially around the opening. In a further embodiment of the invention, first end 111 comprises a plurality of openings, for exposing the contact elements to the pharmaceutical composition.

In one embodiment of the invention, as shown in FIGS. 3A–G, the longitudinal axes of the contact elements 3e are at an angle with respect to the longitudinal axis of the shaft 2, to facilitate access of a contact surface 3 to a tissue site. In one embodiment of the invention, the angle of the contact elements 3e is fixed relative to the longitudinal axis of the neck portion 12 of the contact section 14. In this embodiment, the angle of the contact surface 3e may be modified by detaching one contact section and replacing it with another contact section. However, in another embodiment, the head 11 can pivot about a pivot point in the neck 12 to vary the angle of the contact surface relative to the tissue site. In still another embodiment of the invention, the head 11 is pivotable about the neck 12 but the can be locked into a particular position, e.g., by a screw-like mechanism. In a further embodiment, movement of the head 11 about the pivot point can be controlled remotely through a motor in communication with both the pivot point and a processor.

Contact elements 3e encompassed within the scope of the invention include bristles, fibers, hairs, prongs, tines, and the like. In one embodiment of the invention, the contact elements 3e are bristles with circular or polygonal, flattened, rounded, or shovel-shaped tips 3t. In one embodiment, the bristles are made of natural materials such as horse hair, camel hair, or hog hair, or other types of animal hair; while in another embodiment of the invention, the bristles are synthetic. Preferably, the bristles are capable of effectively retaining a pharmaceutical composition comprising nucleic acids on their surface, but more effectively placing and distributing such a composition at a tissue site. In one embodiment, the bristles are straight; however, in another embodiment, the bristles are irregular or wavy. In one embodiment of the invention, the bristles are thermoplastic and capable of withstanding extremes of temperature.

Suitable synthetic bristle materials encompassed within the scope of the invention include synthetic polyamides which are of sufficient molecular weight to be fiber-forming, such as: polycaprolactam, polyhexamethylene adipamide, polyhexamethylene sebacarnide, the polyamide formed from 1,4,-cis-cyclohexane-bis-methylarnine and adipic acid (see U.S. Pat. No. 3,012,994); the polyamide from m-xylene diamine and adipic acid (see U.S. Pat. No. 2,916,475); the polyamide from 3,5-dimethyl hexamethylene diamine and terephthalic acid (see U.S. Pat. No. 2,752,358); the polyamide from 2,5-dimethyl piperazine and adipyl chloride (see U.S. Pat. No. 3,143,527). Commercial polyamides available include nylon 6,6; nylon 6,10 and nylon 6,12.

Other suitable polymers include polyesters such as polybutylene terephthalate and polyethylene terephthalate. Still other polymers encompassed within the scope of the invention include: polyolefins, such as polyethylene and polypropylene; polyacrylics, such as polyacrylonitrile, polyacrylamide or copolymers of acrylonitrile with methylmethacrylate; polyvinyl chloride or copolymers of vinyl chloride with other vinyl monomers; polymers of fluorinated olefins, such as polytetrafluoroethylene; polystyrene; and the like.

The polymers useful with the bristles of the present invention may be prepared by methods now well known in the art (see, e.g., Notta, Journal of Polymer Science 16: 143–154,1955; U.S. Pat. No. 2,882,263; U.S. Pat. No. 2,874,153; U.S. Pat. No. 2,913,442; U.S. Pat. No. 3,112,300; and U.S. Pat. No. 3,112,301, the disclosures of which are hereby incorporated herein by reference).

In one embodiment, bristles are formed by melt-extruding various thermoplastic polymeric materials through appropriately shaped extrusion orifices following processes such as described in U.S. Pat. No. 2,226,529; U.S. Pat. No. 2,418,482; U.S. Pat. No. 3,745,061; U.S. Pat. No. 3,238,553; U.S. Pat. No. 3,595,952; and U.S. Pat. No. 4,279,053, the entireties of which are incorporated by reference herein. Methods of cutting and shaping bristles are also known in the art and described in U.S. Pat. No. 4,441,227; U.S. Pat. No. 4,688,857; U.S. Pat. No. 5,274,873; U.S. Pat. No. 5,335,389; and U.S. Pat. No. 5,511,275, the disclosures of which are hereby incorporated herein by reference.

The strength and stiffness values of the bristles along with their bend recovery rates (i.e., the time it takes for a bristle to retain a straight position after bending) are optimized to maximize transduction efficiency. As shown in FIG. 5D, transduction of nucleic acids varies with the coarseness of the brush, with optimal expression of nucleic acids at the tissue site obtained with coarse bristles (e.g., horse hair) when compared with a fine bristles (e.g., camel hair). In general, the average molecular weight of the polymer used for these bristles should be in excess of 5,000, 10,000, 20,000, or 30,000, to provide the appropriate strength and stiffness to compress, fold, and/or slightly abrade tissue at a tissue site. As shown in FIG. 5F, transduction efficiency using horse hair bristles is maximal when pressure on the tissue site is light (less than 50% of the bristle length bends), but drops, as pressure increases. The number of times with which the contact surface contacts a tissue site also influences transduction efficiency, increasing from 50% to 100% when 2 to 12 strokes of a contact element comprising a plurality of bristles are used (e.g., providing a ⅛ to ½ inch contact surface).

Stiffness can be controlled by selecting the appropriate diameter of the bristle. In one embodiment of the invention, the diameter of the tip of the bristle is 0.006 inches to 0.04 inches. Other parameters such as tensile strength, and dry and/or wet modulus of the bristles can also be optimized. In one embodiment of the invention, the tensile strength of the bristle ranges from 20 to 70 psi (pounds per square inch). In one embodiment of the invention, the dry stiffness modulus of the bristle ranges from 200 to 600 psi, while the wet stiffness modulus ranges from 50 to 500 psi.

In one embodiment of the invention, as shown in FIG. 3, the contact surface 3 comprises a spongiform material 3C. In one embodiment of the invention, the sponge is affixed directly to the shaft 3 (not shown) by a biocompatible epoxy, and is sufficiently porous to transmit a solution comprising a pharmaceutical composition to a tissue site. In another embodiment, the sponge comprises a plurality of protrusions or contact elements, for contacting a tissue site. Spongiform materials within the scope of the invention, include, but are not limited to, natural sponges, such as Ficulina ficus, Spongilla lacustris, Cliona celata, Spheciospongia vesparia, Halichondria panicea, Stylotella heliophila, Microciona prolifera, Chalina arbuscula, Tetilla laminaris, Hippiospongia, Spongia, Wisconsin spongillinae, Euspongilla lacutris, Meyenia mulleri, Suberites domuncula, Haliclona, Kirkpatrickia variolosa, Latrunculia apicalis, Dendrilla membranosa, or Isodictya crinacea sponges. Synthetic sponges are also encompassed within the scope of the invention, such as chlorovinyl resin sponges produced according to the process disclosed in Belgian Pat. Specification No. 448,061 of Dec. 31, 1942 (Pirelli Societa per Azioni), abstracted at Chemical Abstracts, 1945, column 1571(7), volume 39; cellulosic sponges (cellulose acetate, propionate, butyrate, and mixed esters) produced according to U.S. Pat. No. 2,372,669; sponges formed from organic esters of cellulose and/or polymerized vinyl acetate produced according to the process of Taylor and Gibbins, as disclosed in U.S. Pat. No. 2,223,538; reinforced natural and artificial sponges which are impregnated with a dispersion of rubber as in U.S. Pat. No. 2,257,911; carboxymethylated cellulose sponges, as disclosed by Courtaulds PLC, in PCT Published Pat. Application No. 95/15342, the entireties of which are incorporated herein by reference. In one embodiment, the sponge material forming the contact surface 3 has a plurality of protrusions (i.e., contact elements) for contacting a tissue surface.

In another embodiment of the invention, the contact surface 3 comprises a material through which a liquid or semi-liquid fluid can flow. In this embodiment, the material is a microporous filter material, such as a porous plastic material of the type employed in so-called "felt-tip" pens. Such material is available under a number of brand names, one being provided by Porex Technologies (Fairburn, Ga.). In yet another embodiment of the invention, the contact surface 3 is made of a cotton swab material, such as found in the tip of a Q-tipe®. In yet another embodiment of the invention, the contact surface 3 is made of a fabric such as Gore-Tex®.

Figures 3A, 3B, 3C:
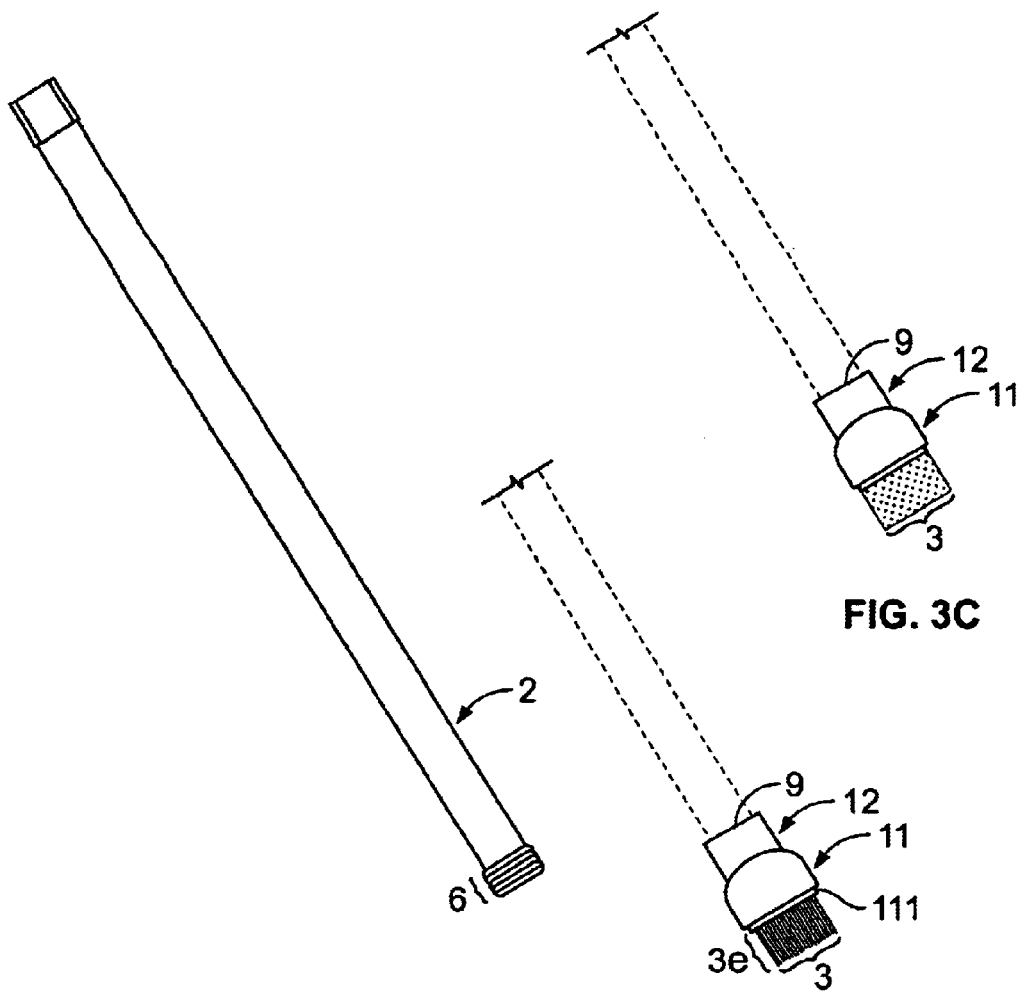
Figure 3H:
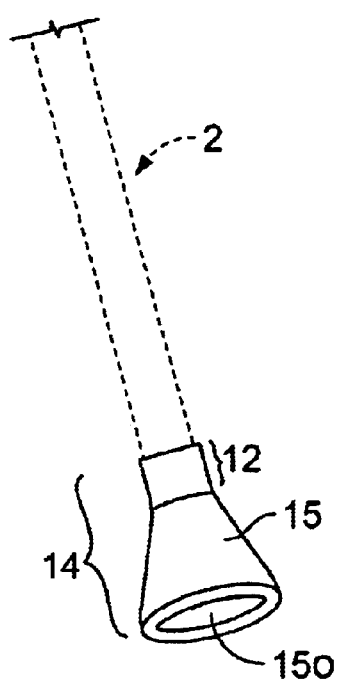
Figure 3I:
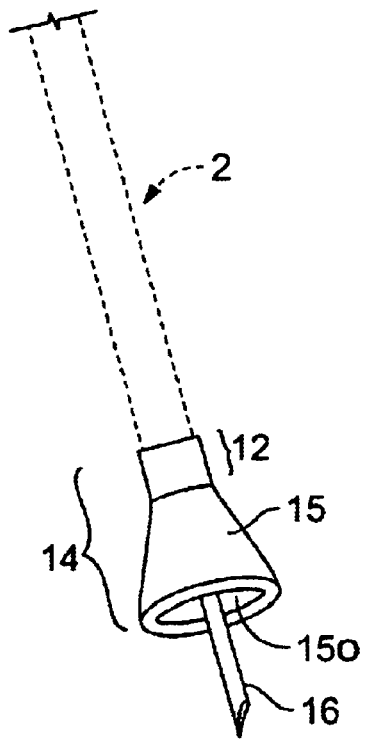

In still another embodiment, shown in FIG. 3H, the contact surface 3 comprises a funnel-shaped extension 15 of the shaft 3 or the neck 12 of the contact section 14 having an opening 15o in the base of the funnel 15. In a further embodiment of the invention, the funnel-shaped extension comprises a spongiform material, or a porous plastic material. In still a further embodiment of the invention, shown in FIG. 3I, the shaft 3 comprises an end (not shown) which communicates with a beveled needle 16 which protrudes through the opening 15o in the base of the funnel. In one embodiment of the invention, the needle 16 is retractable.

The surface area of the contact surface 3 will vary depending on the nature of the tissue site being contacted. For example, in one embodiment of the invention, when the tissue site is the surface of an artery, the contact surface may be from 1/16 to 1/2 of an inch along at least one length (or diameter where the contact surface 3 has a generally circular shape). Similarly, the shape of the contact surface 3 will also vary depending on the tissue site. The smaller the contact surface 3, the more precisely the user is able to localize the pharmaceutical composition (e.g., comprising a therapeutic gene); a larger contact surface 3 may be used when it is desired to transduce a larger tissue site.

The Shaft

In one embodiment of the invention, as shown in FIGS. 1A–B through to 4A–B, the gene delivery device 1 comprises a shaft 2. The shaft 3 comprises a housing defining a lumen 13 and walls providing a graspable surface 25 to allow the user to manipulate the device 1 and move a contact surface 3 coupled to the shaft 3 over a tissue site 4. In one embodiment of the invention, the user directly manipulates the device 1 using his or her hand. In another embodiment, the graspable surface 25 is attached to a guidewire to allow the user to move the contact surface 3 to, and over, a tissue site 4 (e.g., through a medical access device, such as a catheter, endoscope, or laparoscope).

In the embodiment shown in FIG. 2B, where the contact surface 3 can be detached from the shaft 2, the housing comprises a first adapter section 6, for connecting to a contact section 14 comprising the contact surface 3. In this embodiment, the first adapter section 6 comprises threads 8, for threading into a connecting end 9 of the contact section 14 (e.g., such as at the neck 12). However, in another embodiment of the invention, the first adapter section 6 comprises a male or female element for mating with a female or male element at the connecting end 9 of the contact section 14. The shaft 3 further comprises a second adapter section 10 for connecting to a syringe or conduit-tubing or another delivery device (15 in FIG. 1A).

In one embodiment of the invention, the shaft 3 is made of a biocompatible, nonimmunogenic material. Suitable materials include, but are not limited to, polymers, metals, or combinations thereof. Biocompatible and biostable polymers are those which stimulate a relatively low chronic immune response or no immune response. In one embodiment of the invention, at least a portion of the shaft material (>20%) comprises a radiolucent material which may be clear. Suitable polymers can be selected from the group of a polyurethane, a silicone, a polyester, a polyolefin, a polyisobutylene, an acrylate, a vinyl halide polymer (e.g., polyvinyl chloride), a polyvinyl ether (e.g., polyvinyl methylether), a polyvinylidene halide (e.g., polyvinylidene fluoride), a polyacrylonitrile, a polyvinyl ketone, a polyvinyl aromatic polymer (e.g., polystyrene), a polyvinyl ester (e.g., polyvinyl acetate), a polyamide, a polycarbonate, a polyimide, an epoxy resin, an alky resin, a polyoxymethylene, a polyamide/polyether block copolymer, or a combination thereof.

The shaft 3 can also be made from a metal such as stainless steel or a metal alloy such as a nickel-titanium alloy. The shaft 3 can be made from the same or different materials or can be a multilayer construction. For example, a shaft 3 can include a polymeric outer wall surface and a metallic inner wall surface. Polymeric materials encompassed within the scope of the invention include, but are not limited to, polyamide, polyurethane, and/or a polyamide/polyether block copolymers such as commercially available under the trade designation PEBAX (Elf Atochem Corporation, Philadelphia, Pa). In one embodiment, the shaft 3 is disposable; however, in another embodiment, the shaft is sterilizable (e.g., by autoclaving or UV irradiation).

Single-Lumen Shaft

In some embodiments, e.g., as shown in FIG. 4B, the shaft 3 is a solid structure, and the pharmaceutical composition 16 is applied to the contact surface 3 by immersing the contact surface 3 in a solution comprising the pharmaceutical composition 16 or by pipetting or spraying onto the contact surface 3. However, in another embodiment of the invention, shown in FIG. 4C, the shaft 3 comprises a lumen 13 with an opening in proximity to the contact surface 3, and the pharmaceutical composition 16 is delivered to the contact surface 3 through the lumen 13. In one embodiment of the invention, the pharmaceutical composition 16 further comprises a polymerizable compound which polymerizes when the contact surface 3 is contacted to the tissue site 4. For example, in one embodiment the polymerizable compound polymerizes in the presence of ions naturally found in body fluids at the tissue site.

The contact surface 3 can comprise one or a plurality of openings in communication with the opening of the lumen 13. However, in one embodiment, the contact surface 3 comprises a porous material through which the pharmaceutical material 16 can be extruded. In still a further embodiment of the invention, delivery of the composition through the syringe is controlled by a motorized element which creates positive or negative pressure within the body of the syringe.

In one embodiment, the pharmaceutical composition 16 is delivered by attaching another delivery device such as a syringe 15 (with or without conduit-tubing) to adaptor section 10 of the shaft 2, and manually or automatically delivering a measured quantity to the contact surface 3, by exerting a positive or negative pressure within the gene delivery device 1 and shaft 2. In a further embodiment of the invention, delivery of the composition 16 through the syringe 15 is controlled by a motorized element which creates negative pressure within the body of the syringe. In this embodiment, the motorized element can be controlled by a motion of the hand or foot of the operator r (e.g., such as by a foot pedal in communication with the motorized element).

In one embodiment of the invention, the shaft 3 further includes a friable membrane which can be punctured by the delivery device at a preselected time so that the contact surface 3 can be properly positioned and the pharmaceutical composition can be delivered to the lumen 13 of the shaft 3 but prevented from reaching the contact surface 3 until the user actually desires, providing an additional mechanism to fine-tune control of delivery of the pharmaceutical composition 16. In one embodiment, the delivery device 1 comprises a retractable needle for puncturing the membrane within the shaft 2. In still a further embodiment of the invention, the dosage of the pharmaceutical composition 16 is controlled by a processor in communication with an optical system being used to monitor the movement of the contact surface 3 and/or the placement and/or uptake of the pharmaceutical composition 16 at the tissue site 4.

Double-Lumen Shaft

In still another embodiment of the invention, the lumen of the shaft 3 is divided into a first and second channel (13a, 13b) sharing a common wall 13w and the pharmaceutical composition 16 and a polymerizable compound are delivered through the first channel 13a while a polymerizing agent is delivered through the second channel 13b. When the polymerizable composition 16 and pharmaceutical composition and polymerizing agent come into contact with each other at the tissue site 4, the polymerizable composition polymerizes, further localizing the pharmaceutical composition at the tissue site 4. Suitable polymerizable compounds and polymerizing agents include, but are not limited to, fibrinogen and thrombin, alginates and positive ions, hyaluronic acids and crosslinking ions, and collagen and EDC.

In one embodiment, the pharmaceutical composition 16 and polymerizable compound, and polymerizing agent are delivered to the dual channels 13a and 13b of the shaft 3 using a double-barreled syringe (with or without dual-barrel conduit-tubing) which can be used to manually or automatically deliver the pharmaceutical composition 16 to the shaft 2. In still a further embodiment of the invention, additional lumens or channels can be provided within the shaft 3 to deliver other biomolecules to a tissue site (e.g., drugs, antibodies, proteins, hydrogels, and/or other medicaments). However, in other embodiments, these other biomolecules are provided in the same lumen as the pharmaceutical composition 16 and are either provided simultaneously or at different times as the pharmaceutical composition 16.

In one embodiment of the invention, mixing of the polymerizing agent and polymerizable compound is performed at the distal end of the shaft 3 (e.g., just proximal to the contact surface 3) by providing micropores in portions of the common wall 13w of the shaft 3 at the distal end of the shaft 2.

Surface Coatings

The shaft 3 and/or contact surface 3 can be coated with agents to minimize adhesion of the pharmaceutical composition 16 to the contact surface 3 and/or shaft 2. Suitable anti-adhesive agents which can be used depend on the type of nucleic acid present in the pharmaceutical composition 16. For example, in one embodiment where the pharmaceutical composition 16 comprises naked DNA, a suitable DNA-repelling agent such as silane is used. In an embodiment of the invention where the nucleic acid is encapsulated with viral glycoproteins, the agent is a positively charged molecule such as polylysine. In an embodiment where the nucleic acid is encapsulated within a polycationic liposome, the agent comprises negatively charged molecules. While harmful effects from temporarily introducing a gene delivery device into the body should be minimal, in further embodiments of the invention the shaft 3 and/or contact surface 3 are coated with agents to minimize these effects. For example, in one embodiment, the shaft 3 and/or contact surface 3 is/are coated with an anticoagulant such as heparin to prevent blood from clotting around the shaft 3 and/or contact surface 3, particularly in settings where the gene delivery device 1 is introduced through a medical access device such as a catheter, endoscope, or laparoscope. In still a further embodiment of the invention, the shaft 3 and/or contact surface 3 is/are coated with a medicament such as an antibiotic, anti-inflarnmatory agent, drug, or other therapeutic molecule. In embodiments where the shaft 3 comprises a lumen 13 or channels 13a and 13b, the walls of the lumen or channels can also be coated.

Radiopaque Markers

In one embodiment, at least a portion of the gene delivery device 1 comprises a radiopaque material. Radiopaque materials encompassed within the scope of the invention include, but are not limited to, iodine compounds, barium compounds, gallium compounds, thallium compounds, and the like. The radiopaque material can be mixed with the polymeric material forming the shaft 3 and/or contact section 14, or can be affixed to the shaft 3 and/or the contact section using a biocompatible adhesive, or embedded within a notch within a portion of the shaft 3 or contact section 14. In one embodiment of the invention, the shaft 3 comprises at least one radiopaque ring surrounding its circumference. In another embodiment, the shaft 3 comprises a linear radiopaque marker aligned with its longitudinal axis.

The radiopaque marker provides a means to localize, orient, and monitor movement or position of the gene delivery device 1, particularly when it is being inserted into the body thorough a medical access device. In one embodiment, the medical access device also comprises a radiopaque marker and movement of the gene delivery device 1 is monitored by comparing the distance of a radiopaque marker on the shaft 3 of the gene delivery device 1 from the (reference) marker on the medical access device. In another embodiment, where head 11 of a contact section 14 can pivot, the angle of the contact surface 3 with respect to a tissue site can be monitored by monitoring the position of a radiopaque marker on the head 11 relative to the position of a radiopaque marker on the shaft 2, or on the medical access device.

Adapting the Gene Delivery Device for Use with a Medical Access Device

In one embodiment, the gene delivery device 1 is positioned at a tissue site 4 using a medical access device. In one embodiment, therefore, the shaft 3 is adapted for the application of force by a guidewire. For example, in one embodiment, the shaft 3 comprises a guidewire lumen through which the guidewire can be inserted. In another embodiment, the shaft 3 comprises a ring, or series of rings through which a guidewire can be inserted. The ring(s) can be an integral part of the shaft surface 2s or can be removable from the shaft 2.

In still a further embodiment of the invention the shaft 3 can be adapted to provide an illumination source for illuminating a tissue site 4, e.g., by providing optical fiber(s) within a lumen in the shaft 3 or attached to the outside of the shaft 2. Additionally, one or more light-directing elements can be provided in communication with a light source and the contact surface 3 for directing light from the light source to the contact surface 3 and/or tissue site 4 and for receiving light transmitted from the contact surface 3 and/or tissue site 4. The light-directing elements can be used in conjunction with other optical elements (e.g., optical fibers) within the medical access device to allow the user to obtain visual information from the contact surface 3 and/or tissue site 4, and enabling the user to better control positioning of the contact surface 3 relative to the tissue site 4.

The Pharmaceutical Composition

Nucleic Acids

In one embodiment of the invention, the pharmaceutical composition 16 comprises a nucleic acid which is selected from the group consisting of DNA, RNA, anti-sense molecules, triple-helix-forming nucleic acids, aptamers, ribozymes, and combinations thereof. In another embodiment of the invention, the nucleic acid is encapsulated, such as by viral proteins or by a liposome coat. In a further embodiment of the invention, the nucleic acid is an adenoviral vector encapsulated by adenoviral glycoproteins, and transduction of cells at the tissue site 4 includes infection by the adenovirus. In still a further embodiment of the invention, the nucleic acid is bound to or associated with a targeting molecule which binds to a cell at the tissue site.

The choice of biological vehicle can be broadly divided into "viral" vs. "non-viral" vs. "hybrid" vectors (O'Brien, Journal of the Irish Colleges of Physicians and Surgeons 27: 33–39,1998; Dyer, et al., Molecular Therapy 1: 213–224, 2000; Heistad, et al., supra; Richter, et al., Genomics 2: 117–127,2000). Each class of vector has a characteristic profile relating to nucleic acid integration, efficiency of transduction, cell avidity, and induced inflarnmatory response.

Viral Vectors

Viral vectors encompassed within the scope of the invention include, but are not limited to, RNA viruses (retroviridae) such as mouse Moloney leukemia virus (MoMLV) or lentiviruses including human (HIV), bovine (BIV), and simian (SIV) immunodeficiency viruses. DNA viral vectors include, but are not limited to, strains linked to the "common cold" pathogen (adenovirus) or parvoviruses (such as adeno-associated virus, AAV). Incorporation into the host-cell genome (DNA integration) following entry into the nucleus is a feature of RNA viruses such as MoMLV and HIV, and the DNA-containing AAV, but is not a feature of adenoviral infection as adenoviral nucleic acids remain epichromosomal. Although the benefit of DNA integration is relatively long-term recombinant gene expression, the trade-off is a higher risk of insertional mutagenesis (O'Brien, supra). With regards to the type of cell type infected by viruses, MoMLV exclusively targets dividing cells, while lentiviruses can transduce some, but not all types of dividing and nondividing cells. Adenoviruses can infect an even wider range of cell types.

Adenoviruses

Recombinant adenoviral vectors have been used to transfer one or more recombinant genes to diseased cells or tissues in need of treatment. As discussed by Crystal (Science 270:404–410,1995), adenoviral vectors can be produced in high titers (i.e., up to $10^{18}$ viral particles/mL), and can efficiently transfer genes to nonreplicating, as well as replicating, cells.

At present, there are 49 human adenoviral serotypes known, categorized into 6 subgenera (A through F) based on nucleic acid sequence, fiber protein characteristics, and other biological properties (Crawford-Miksza, et al., Journal of Virology 70: 1836–1844,1996). Group C viruses (e.g., serotypes 2 and 5, or Ad2 and Ad5) have been predominantly used in gene transfer studies, including human gene therapy trials (see, e.g., Rosenfeld, et al., supra; Rosenfeld, et al., Cell 68: 143–155,1992; Crystal, et al., Nature Genetics 8: 42–51,1994; Yei, et al., Gene Therapy 1: 192–200,1994; Chen, et al., supra). Other groups and serotypes include, but are not limited to: group A (e.g., serotypes 12 and 31), group B (e.g., serotypes 3 and 7), group D (e.g., serotypes 8 and 30), group E (e.g., serotype 4) and group F (e.g., serotypes 40 and 41). The structure of adenoviruses is described by Pettersson (In: The Adenoviruses, pp. 205–270, Ginsberg, ed., Plenum Press, New York, N.Y., 1984), and by Roberts, et al. (Science 232: 1148–1151,1986) and Boudin, et al. (Virology 92: 125–138, 1979), the entireties of which are incorporated herein by reference.

A great advantage of adenoviruses is their broad cell avidity, while their disadvantages include a propensity to induce an inflammatory response in vivo and relatively short-lived gene expression (Newman, et al., Journal of Clinical Investigation 96: 2955–2965, 1995; Thomas, et al., PNAS 97: 7482–7487, 2000; Vassalli, et al., Circulation Research (Online) 85: e25–e32, 1999; Wen, et al., Arteriosclerosis, Thrombosis, and Vascular Biology 20: 1452–1458, 2000; Wood et al., Trends in Neurosciences 19: 497–500, 1996; Chen et al., supra). These disadvantages can be circumvented by administering different serotypes as doses are repeated or, more appropriately, by using "gutted" adenoviruses (containing minimal native viral genome) which represent significantly less immunogenic and cytotoxic vectors (Brenner, et al., Molecular Therapy 1: 205, 2000; Dyer, et al., supra; Von der Leyen, et al., PNAS 92: 1137–1141,1995).

Recombinant adenovirus comprising chimeric coat protein(s) that have a decreased ability or inability to be recognized by antibodies (i.e., neutralizing antibodies) directed against the corresponding wild-type adenovirus coat protein can also be used (see, e.g., as disclosed in U.S. Pat. No. 6,127,525, the entirety of which is incorporated by reference herein). In one embodiment, delivery of adenoviral vectors to a site is facilitated by precipitating the adenovirus with calcium phosphate crystals (see, e.g., as disclosed by Toyoda, et al., Gene Therapy 7: 1284–1291,2000).

To date, the adenovirus (particularly serotype 5) remains the predominant vector used in cerebrovascular gene transfer studies, most likely due to its broader cell avidity, greater efficiency of transduction, and ability to be generated in relatively high titers (i.e., between $10^{11}$–$10^{12}$ PFU/mL; Chen, et al., supra; O'Brien, supra). When used in gene transfer, the adenoviral genome is combined with a gene of interest whose expression (i.e., transcription followed by translation into a particular protein) is driven by a promoter, such as cell-nonspecific promoter obtained from CMV, or a cell-specific promoter such as SM22α (specific for smooth muscle cells; Kim, et al., supra). The adenovirus is rendered replication-incompetent through the deletion of certain replication-associated genetic sequences (e.g., "early" regions E1 and E3; Heistad, et al., supra; Chen, et al., supra;

Spector, et al. In: *Viral Gene Techniques: Methods in Molecular Genetics* (Vol. 7), pp. 31–44, Cole, ed., Academic Press, San Diego, Calif., 1995). Entry of the modified virus into target cells typically involves attachment of the viral fiber knob to the host-cell plasmalemma, facilitated by CAR (Bergelson, et al., Science 275: 1320–1323, 1997), and is followed by $\alpha_v$-integrin-mediated internalization (Wickham, et al., Cell 73: 309–319, 1993). Once it has entered the cell, the adenovirus retains an epichromosomal (nonintegrated) position in the nucleus, and uses the biosynthetic machinery of the host to generate the (recombinant) protein of interest. In experimental models, expression of recombinant proteins is detectable morphologically, biochemically, and functionally (Blau, et al., New England Journal of Medicine 333: 1204–1207, 1995; O'Brien, supra; Heistad, et al., supra; Richter, et al., supra; Newman, et al., supra; Thomas, et al., supra; Vassalli, et al., supra; Wood, et al., supra, Chen, et al., supra, the entireties of which are incorporated by reference).

Naked DNA

In one embodiment of the invention, the genetic material delivered to a issue site 4 is in the form of a plasmid or naked DNA. Plasmids are autonomous, self-replicating extrachromosomal, circular strands of DNA. They can modified to contain a promoter which drives expression (albeit transient) of a gene encoding a protein of interest (Chen, et al., supra). Less commonly, plasmids can be integrated or partly integrated in the host-cell genome, an event associated with their stable expression. Episomal plasmid vectors are nonintegrated plasmids able to replicate in the nucleus of transfected cells and therefore be expressed in a total growing cell population. Plasmid preparation is routine in the art and disclosed in the work of Spector, et al. (supra) and Chen, et al. (supra).

Liposomes

Lipid particles have been shown to be efficient vehicles for in vivo gene delivery applications. Lipid particles complexed with DNA (i.e., plasmid-liposome complexes) have been used in vivo to express therapeutic genes (Nabel, et al., supra; Wang, et at., PNAS 84: 7851–7855, 1987; Zhu, et al., Science 261: 209–211,1993; Soriano, et al., PNAS 80: 7128–7131, 1983). In particular, Lipofectin™ (Gibco BRL, Gaithersburg, Md.) has been successfully used for the transduction of various cell lines in vitro for systemic gene expression after intravenous delivery into adult mice (Felgner, et al., PNAS 84: 7413–7417, 1987; Zhu, et al., supra, the entireties of which are incorporated herein by reference).

In embodiments of the invention, therefore, pharmaceutical compositions comprising sense or antisense nucleic acids or nucleotides are complexed to lipid particles (see as disclosed in Leonetti, et al., PNAS 87: 2448–2451, 1990; Burch, et al., Journal of Clinical Investigation 88:1190–1196, 1991; Thierry, et al., Nucleic Acids Research 20: 5691–5698,1992; Wang, et al., supra; Zhu, et al., supra, the entireties of which are incorporated herein by reference). In one embodiment, the lipid particle is formed using the cationic lipid DOTMA, N[1-(2,3-dioleyloxy)propyl]-N,N, N-trimethyl-ammonium chloride, and DOPE, dioleylphosphatidyl ethanolamine, at a 1:1 molar ratio (e.g., Lipofectin™). The lipidic particles prepared with this formulation spontaneously interact with DNA through the electrostatic interaction of the negative charges of the nucleic acid moieties and the positive charges at the surface of the cationic lipid particles. The DNA/liposome-like complex fuses with tissue culture cells thereby facilitating the intracellular delivery of functional (exogenous) DNA (see, e.g., Feigner, et al., supra, incorporated by reference herein).

In another embodiment, Lipofectamine™ (Gibco BRL), composed of DOSPA, 2,3-dioleyloxy-N[2 (sperminecarboxamido)ethyl]-N,N-dimethyl-1-propanaminium trifluoracetate, and DOPE at a 1:1 molar ratio, is complexed with nucleic acids. In still another embodiment, Lipofectace™ (Gibco BRL) composed of DDAC, dimethyidioctadecylarnmonium chloride, and DOPE at a 1:1 molar ratio can also be used.

In another embodiment, lipopolyamines (e.g., DOGS, dioctadecylamidoglycine-spermine; spermine-5-carboxy-glycinediotade-cylamide) are complexed with nucleic acids (see, e.g., Behr, et al., PNAS 86: 6982–6986, 1989; Barthel, et al., DNA Cell Biology 12: 553–560, 1993). Lipopolyamines are synthesized from a natural polyamine, spermine, chemically linked to a lipid. For example, DOGS is made from spermine and dioctadecylarnidoglycine (Behr, et al., supra, incorporated herein by reference). DOGS spontaneously condenses DNA on a cationic lipid layer resulting in the formation of nucleolipidic particles. This lipospermine-coated DNA shows high transduction efficiency (Barthel, et al., supra). In still a further embodiment, the lipid portion of the lipid-nucleic acid complex comprises a multitude of different types of lipid molecules. Therefore, in one embodiment, the lipid portion of the lipid-nucleic acid complex comprises a cationic lipopolyamine and a neutral lipid.

Hybrid vectors can also be provided and are encompassed within the scope of the invention. Such vectors include, but are not limited to, virus-liposome complexes (see, e.g., Von der Leyen et al., supra).

Antisense Nucleic Acid Molecules

In one embodiment of the invention, the pharmaceutical composition 16 comprises antisense nucleic acids which are complementary to a target mRNA which the user desires to block expression of. Techniques of generating antisense constructs are described in, for example, C. A. Stein, et al., Cancer Research 48: 2659–2668, 1988; Walder, Genes & Development 2: 502–504, 1988; Marcus-Sekura, Anal. Biochemistry 172: 289–295, 1988; G. Zon, Journal of Protein Chemistry 6: 131–145, 1987; Zon, Pharmaceutical Research 5: 539–549, 1988; Van der Krol, Mol, & A. R. Stuitje, BioTechniques 6: 958–973, 1988; and Loose-Mitchell, TIPS 9: 4547, 1988, the entireties of which are incorporated by reference. In another embodiment, the antisense nucleic acids delivered by the gene delivery device 1 are modified to enhance the stability of the nucleic acids. Suitable modifications are described by Agrarwal, et al., PNAS 85: 7079, 1988; Sarin, et al., PNAS. 85: 7448, 1988, for example, the entireties of which are incorporated herein by reference.

Ribozymes

In a further embodiment, the pharmaceutical composition 16 delivered by the gene delivery device 1 comprises ribozyme nucleic acid molecules. Ribozymes are enzymatic RNA molecules which can be designed to cleave a target mRNA, for example, an mRNA encoding a deleterious gene product. In general, ribozymes act by binding to a target RNA through complementary base-pairing and cleaving target RNA, preventing the RNA from directing the synthesis of an encoded protein. The ribozyme functions catalytically in that it can repeatedly bind and cleave new targets. Because single mismatches, or base-substitutions, near the site of cleavage can completely eliminate catalytic activity of a ribozyme, ribozyme nucleic acids are highly specific in their effects (see, e.g., Woolf, et al., PNAS 89: 7305–7309, 1992). Sequences for use in constructing ribozyme vectors are described in, for example, Rossi, et al., 1992 Aids Research and Human Retroviruses 8: 183, 1992; Hampel and Tritz, Biochemistry 28: 4929, 1989; and Hampel, et al., Nucleic Acids Research 18: 299, 1990; Perrotta, et al., Biochemistry, 31: 16, 1992; Guerrier-Takada, et al., Cell 35: 849, 1983; Collins, et al. 1990 Cell 61: 685–696; Saville and Collins, PNAS 88: 8826–8830; Collins and Olive, Biochemistry 32: 2795–2799, 1983; and Cech, et al., U.S. Pat. No. 4,987,071; Scanlon et al., PNAS 88: 10591–5, 1991; Dropulic et al., J Virol. 66: 1432–41, 1992; Weerasinghe, et al., J Virol. 65: 5531–5534, 1991; Ojwang, et al., PNAS 89: 10802–10806, 1992; and Chen, et al., Nucleic Acids Res., 20: 4581–1589, 1992; Sarver, et al., Science, 247, 1222–1225, 1992, the entireties of which are incorporated herein by reference.

It should be obvious to those of ordinary skill in the art that any nucleic acid vector currently employed in nucleic acid-based therapies, or developed for use in these therapies, can be used with the gene delivery device 1 according to the invention, and that these vectors are encompassed within the scope of the invention.

Choice of Sequence

The choice of sequence of the nucleic acid contained in the pharmaceutical composition 16 depends on the desired protein to be expressed in a target tissue site 4 and the type of nucleic acid vector. For example, in one embodiment, the nucleic acid comprises at least a coding sequence for a gene of interest. In another embodiment, the nucleic acid comprises coding sequences for multiple genes of interest. However, in another embodiment, the nucleic acid comprises an antisense sequence for altering expression of an endogenous gene sequence. In still another embodiment, the nucleic acid comprises catalytic sequences (e.g., encoding ribozymes). In a further embodiment, the nucleic acid comprises sequences which bind to molecules not naturally bound by nucleic acids (e.g., the nucleic acid is an aptamer which achieves a therapeutic effect by binding to a protein or other biomolecule). The encoded sequence can be any gene sequence expressing a full length protein or a polypeptide or oligopeptide. In one embodiment, the coding sequence encodes a protein or polypeptide expressed in, or bioactive at: cardiovascular tissue (e.g., vascular endothelial growth factor); neural, glial, choroidal, or ependymal tissue; connective tissue; cardiac, smooth, or skeletal muscle; intact or wounded skin; joint cartilage or synovial tissue; liver; spleen; pancreas; kidney; adrenal gland; stomach; colon; lung; lymphatic tissue; and other tissues. In one embodiment, the coding sequence encodes a tumor suppressor molecule such as p53, retinoblastoma protein, or other cell cycle proteins or polypeptides. In another embodiment, the coding sequence encodes a protein or polypeptide involved in vasomotor function such as a nitric oxide synthase isoform (e.g., constitutive eNOS, or its inducible counterpart, INOS), or an isoform of endothelin, cyclooxygenase, superoxide dismutase, or heme-oxygenase (see, e.g., Heistad, et al., supra; Khurana, et al., Journal of Clinical Neuroscience 4: 122–131, 1997; Onoue, et al., Journal of Cerebral Blood Flow and Metabolism 19: 1029–1037,1999; Suzuki, et al., Journal of Clinical Investigation 104: 59–66, 1999; Toyoda, et al., American Journal of Physiology 278: H586–H594, 2000, the entireties of which are incorporated herein by reference).

In another embodiment of the invention, the sequence provided is a regulatory sequence, such as a promoter sequence or enhancer sequence, e.g., for preventing transcriptional regulators from binding to an endogenous promoter or enhancer sequence by competing with that sequence for binding with the regulator. In still another embodiment, an anti-regulatory sequence is provided, e.g., a sequence of at least 10 partially complementary or fully complementary nucleotides which prevent a regulator protein from binding by competing for the target site.

Targeting Molecules

In one embodiment, the nucleic acids are complexed to targeting molecules which bind to specific cells or to other biomolecules which provide a therapeutic effect. Lipid particles can be complexed with virtually any biological material including, but not limited to, proteins, therapeutic agents, and chemotherapeutic agents, and provide a useful delivery system for such agents. Therefore, in one embodiment, a targeting molecule is complexed to a lipid particle which in turn is complexed to a nucleic acid. However, in another embodiment, a targeting molecule or other biomolecule is directly conjugated to the nucleic acid, e.g., via complementary or "sticky-end" binding to a 5' or 3' terminal of the nucleic acid as per methods of conjugating biomolecules directly to nucleic acids widely known in the art. In one embodiment of the invention, the targeting molecule is a ligand for a receptor or protein expressed on abnormally proliferating cells, such as cancer cells. In a further embodiment of the invention, the targeting molecule is a ligand for a receptor or protein expressed selectively on a target tissue belonging to a diseased organ (e.g., atheromatous, inflamed, or spastic cardiovascular tissue; degenerative or inflamed neural, muscular, or skin tissue, and others). Such types of targeting molecules include, but are not limited to antibodies.

The gene delivery device 1 may be used to provide gene therapy by itself or in conjunction with other therapies. For example, in one embodiment, gene delivery is performed at the same time that a patient is being treated by radiation, chemotherapy, or other drug therapies. The gene delivery device 1 may be used to deliver drugs and other medicaments in addition to nucleic acids to a tissue site 4, either providing such drugs and medicaments through a lumen of the shaft 2, allowing the contact surface 3 to function as an applicator which also localizes and places the drug or other medicament at the tissue site 4, and/or by coating the shaft 2 and/or contact surface 3 with the drug or other medicament. The drug or other medicament can be provided at the same time or at different times as the pharmaceutical composition 16 comprising the nucleic acid.

The efficacy of gene transfer at a tissue site 4 can be determined by monitoring the expression of a marker protein encoded by the nucleic acid provided in the pharmaceutical composition 16 as discussed above, or by monitoring the uptake of a vital dye.

However, in another embodiment of the invention, the efficacy of gene transfer is monitored by observing one or multiple clinicotherapeutic endpoints (e.g., decreased prostate- specific antigen levels in the case of prostate cancer, increased mobility in the case of peripheral vascular disease, decreased pain in the case of some cancers or neurological disorders) in treated as compared with untreated patients, or patients exposed to the pharmaceutical composition 16 without the use of the gene delivery device 1. In still another embodiment of the invention, expression of a therapeutic gene itself may be monitored, e.g., by biopsy of a tissue segment at the tissue site 4, or by measuring the presence of the therapeutic gene product in the circulation, if it is a secreted protein.

In a further embodiment, a delivery device 15 is provided for attachment to the shaft 2, such as a syringe (e.g., a double-barreled syringe) and/or single- or multi-lumen conduit-tubing and/or other components for facilitating use or attachment of the device 15 to the shaft 2.

Detectable Moieties

In still another embodiment of the invention, the pharmaceutical composition 16 comprises a solution which comprises detectable moieties, and placement and localization of the pharmaceutical composition 16 at the tissue site 4 is monitored by detecting the detectable moieties. In one embodiment of the invention, the solution comprises GFP. In another embodiment of the invention, the solution itself is radiopaque, e.g., comprised of a biocompatible contrast material such as iodine. In a further embodiment, the solution comprises a vital dye which can be taken up by cells along with nucleic acids and visualized using the naked eye or an optical system provided in communication with the contact surface 3. Suitable dyes encompassed within the scope of the invention include those commercially available from Molecular Probes (Eugene, Oreg.). In still a further embodiment, a marker protein is encoded by a nucleic acid within the pharmaceutical composition 16 and expression of the marker protein in the circulation or target tissue is monitored to assess the uptake of the pharmaceutical composition. Thus, in one embodiment, nucleic acids expressing GFP or β-galactosidase are provided within the pharmaceutical composition 16.

Method of Using a Gene Delivery Device

The invention provides a device and method for augmenting the efficacy of gene transfer by localizing a vector at a tissue site and by increasing the uptake of the vector by cells at the tissue site. In one embodiment, the invention provides a method for delivering a pharmaceutical composition 16 comprising a nucleic acid to a tissue site 4. The method comprises the steps of providing a gene delivery device 1 comprising a contact surface 3, and applying the pharmaceutical composition 16 to the contact surface 3. The contact surface 3 is then contacted to the tissue site 4, thereby placing and localizing the pharmaceutical composition 16 at the tissue site 4. Contact with the tissue by the contact surface 3 bearing the pharmaceutical composition 16 significantly enhances transduction of the tissue by the nucleic acid relative to transduction of noncontacted tissue to which the pharmaceutical composition is applied, e.g., by pipetting or "dripping", immersing, spraying, injecting, or any other known dispensing means. In one embodiment of the invention, transduction efficiency is enhanced 10-fold.

In one embodiment of the invention, contacting is performed by moving the contact surface 3 across the tissue site 4, such as by a back and forth and/or circular motion. In one embodiment, the contacting compresses tissue at the tissue site relative to noncontacted tissue, while in another embodiment, the contacting causes a portion of the tissue site to temporarily lie over another portion of the tissue site (e.g., ruffling the tissue). In still another embodiment of the invention, cells at the tissue site are abraded in the process of contacting.

In one embodiment of the invention, the tissue site 4 is selected from the group consisting of, but is not limited to, the outer or inner surface of a blood vessel, skin, wounded tissue, mucosa, the outer or inner surface of an abdominal or thoracic or special sensory organ, the cortical or ventricular surface or parenchyma of the brain, the spinal cord or its surrounding tissue, meningeal tissue, a muscle, tendon, cartilage, joint, or bone. In one embodiment, the tissue site 4 is cerebrovascular tissue. In another embodiment, the tissue site 4 is cardiovascular tissue.

In one embodiment, contact is with a surface which is naturally exposed (e.g., skin, or oral or vaginal mucosa) and the contact surface 3 is used to apply a pharmaceutical composition 16 topically. In one embodiment, e.g., skin infected with papilloma virus is contacted with a pharmaceutical composition 16 comprising nucleic acid or antisense molecules which prevent the expression of papilloma viral proteins.

In another embodiment of the invention, the tissue site 4 is contacted with the contact surface 3 through an open surgical field. For example, in one embodiment, the tissue site 4 is exposed during neurosurgery (e.g., for tumors); cardiovascular, cardiothoracic or peripheral vascular surgery for cardiac, pulmonary, coronary, carotid, aortic or peripheral vascular indications (e.g., such as coronary or peripheral artery disease); orthopedic surgery; gastrointestinal, endocrine, or colorectal surgery; surgery of the eyes, ears, nose and throat, and the like.

In another embodiment, the contact surface 3 of the gene delivery device 1 is inserted into the lumen of an organ, body cavity, or vessel prior to contacting the tissue site 4 such as by using a medical access device. Medical access devices may be used to guide the gene delivery device to the tissue site 4 during minimal-access surgery, such as keyhole surgery (e.g., abdominal laparoscopic surgery; thoracoscopy; or neurosurgical ventriculoscopy).

The medical access device can also be used in other interventional procedures, including, but not limited to, upper and lower endoscopy, thoracoscopy, laparoscopy, ventriculoscopy, arthroscopy, oropharyngolaryngoscopy, otoscopy, and ophthalmoscopy, and intra/transluminal cardiovascular interventions.

"Keyhole surgery" is a procedure which involves forming a small (keyhole) opening in the skin and inserting a medical access device through the keyhole. Visualization of movement of the access device is carried out using a camera ("scope") inserted locoregionally (e.g., in sufficient proximity to be able to monitor movement of the medical access device) through a separate keyhole. Alternatively, the medical access device and/or gene delivery device 1 themselves can be equipped with optical imaging capabilities (e.g., by providing one or more optical fibers in communication with either or both devices and providing light-directing elements, e.g., lenses and mirrors, in communication with the optical fibers).

In one embodiment, the gene delivery device 1 is positioned at a tissue site 4 by using a guidewire to first position a medical access device in proximity to the tissue site 4; here, monitoring positioning of the access device may be performed by observing the movement of a radiopaque marker on the access device. The gene delivery device 1 is then inserted into a lumen within the medical access device using a guidewire which fits into a guidewire lumen of the shaft 3 of the gene delivery device 1 or ring(s) on the outside of the shaft 3 to push and position the gene delivery device 1 in proximity to the tissue site 4. In one embodiment, movement of the gene delivery device 1 is monitored by observing the position of radiopaque marker(s) on either, or both, of the contact section 14 or shaft 3 of the gene delivery device 1.

In one embodiment, where the contact surface 3 is to contact a tissue surface facing a forward-end opening in the medical access device, the contact surface 3 is at a 180° angle relative to the longitudinal axis of the shaft 3 (see FIG. 3G). However, in another embodiment, where the tissue site 4 is parallel to the longitudinal axis of the medical device and shaft 3 of the gene delivery device 1, the contact surface is at a 90° angle relative to the longitudinal axis of the shaft 3 (see FIG. 3F). Other angled configurations of the contact surface 3 can be provided (see, e.g., FIGS. 3D and 3E).

In one embodiment, the contact section 14 is removable from the shaft 2, allowing the user to select suitably angled contact sections 14 for particular purposes. However, in another embodiment, the head 11 of the contact section 14 can pivot about a pivot point and this pivoting can be manually controlled, or remotely controlled through a motor in communication with the pivot point (e.g., a galvanometer, servomotor) enabling the user to control the movement of the contact surface 3 relative to a tissue site 4.

In still a further embodiment of the invention, the contact surface 3 is in communication with an optical system including a light source, a light-transmitting element (e.g., one or more optical fibers), one end of which is in proximity to the contact surface 3, and a detector in communication with the light-transmitting element. In this embodiment, contacting of the contact surface 3 with the tissue site is monitored by detecting light transmitted from the light source through the transmitting element. In the embodiment of the invention where the pharmaceutical composition 16 comprises a solution which comprises detectable moieties (e.g., GFP and the like), placement and localization of the pharmaceutical composition 16 can also be monitored. In one embodiment of the invention, the compression or folding of tissue is monitored. In still another embodiment, the placing and/or uptake of the pharmaceutical composition is monitored. In a further embodiment of the invention, the monitoring of the compression or folding of tissue and/or of the placing and/or uptake of the pharmaceutical composition is used to determine whether further contacting is necessary.

In still a further embodiment, the medical access device comprises a cutting element, and a tissue site is exposed to the contact surface 3 by the cutting element, prior to contacting with the contact surface 3. In one embodiment, the cutting element is a laser. In another embodiment, the cutting element is an ultrasonic pulse.

The gene delivery device 1 may be used to provide gene therapy alone or in conjunction with other therapies. For example, in one embodiment, gene delivery is performed at the same time that a patient is being treated by radiation, chemotherapy, or other pharmacotherapies. The gene delivery device 1 may be used to deliver drugs and other medicaments in addition to nucleic acids to a tissue site 4, either providing such drugs and medicaments through a lumen of the shaft 2, allowing the contact surface 3 to function as an applicator which also localizes and places the drug or other medicament at the tissue site 4, and/or by coating the shaft 3 and/or contact surface 3 with the drug or other medicament. The drug or other medicament can be provided at the same time or at different times as the pharmaceutical composition 16 comprising the nucleic acid.

The efficacy of gene transfer at a tissue site 4 can be determined by monitoring the expression of a marker protein encoded by the nucleic acid provided in the pharmaceutical composition 16 as discussed above, or by monitoring the uptake of a vital dye. However, in another embodiment of the invention, the efficacy of gene transfer is monitored by observing one or multiple clinicotherapeutic endpoints (e.g., decreased prostate-specific antigen levels in the case of prostate cancer, increased mobility in the case of peripheral vascular disease, decreased pain in the case of some cancers or neurological disorders) in treated as compared with untreated patients, or patients exposed to the pharmaceutical composition 16 without the use of the gene delivery device 1. In still another embodiment of the invention, expression of a therapeutic gene itself may be monitored, e.g., by biopsy of a tissue segment at the tissue site 4, or by measuring the presence of the therapeutic gene product in the circulation if it is a secreted protein.

In a further embodiment, another delivery device 15 is provided for attachment to the shaft 3 of the gene delivery device 1, such as a syringe (e.g., a double-barreled syringe) and/or single- or multi-lumen conduit-tubing and/or other components for facilitating use or attachment of the device 15 to the shaft 2.

Kits

In one embodiment, kits are provided to facilitate performing the gene delivery method. In one embodiment, the kit comprises a gene delivery device 1 comprising a contact surface 3 for contacting a tissue, a graspable surface 2s for attachment to a contact surface, at least one contact surface 3 for attachment to the graspable surface 2s, and a pharmaceutical composition 16. In another embodiment, the kit comprises a gene delivery device 1 comprising a contact surface 3 for contacting a tissue, a graspable surface 2s for attachment to a contact surface, at least one contact surface 3 for attachment to the graspable surface 2s, and a pharmaceutical composition 16 comprising a nucleic acid. In one embodiment of the invention, the gene delivery device 1 comprises a shaft 3 for attachment to a contact section 14, and a plurality of angulated contact sections 14. Irt one embodiment of the invention the gene delivery device is a brush, such as a paintbrush or a toothbrush, or a brush with radially projecting bristles or fibers.

In one embodiment of the invention, the pharmacological composition consists of a the nucleic acid within the pharmaceutical composition are selected from the group consisting of DNA, RNA, anti-sense molecules, triple-helix-forming nucleic acids, aptamers, and ribozymes. In another embodiment of the invention, the nucleic acid is a viral vector, such as an adenovirus, adeno-associated virus, or retrovirus. In still another embodiment of the invention, the kit includes helper molecules or cells for amplifying the adenoviral vector and for providing a renewable source of the pharmaceutical composition. In still another embodiment, a coating for the gene delivery device 1 is provided either on the device itself or separately. In one embodiment, the coating is silane; in another embodiment the coating is polylysine.

In a further embodiment of the invention, the kit includes a polymerizeable compound and a polymerizing agent, for enhancing localization of the nucleic acid at the tissue site. In another embodiment of the invention, the polymerizeable compound is fibrinogen and the polymerizing agent is thrombin. In a further embodiment of the invention, the pharmaceutical composition 16 comprises detectable moieties (e.g., GFP, or a dye, or radiopaque particles), while in a further embodiment of the invention, the kit comprises a solution of detectable moieties which can be added to the pharmaceutical composition. In still another embodiment, a nucleic acid expressing a detectable marker protein (e.g., GFP or β-galactosidase) is provided.

In one embodiment of the invention, the gene delivery device within the kit comprises a graspable surface 2s having a longitudinal axis, and the contact surface 3 is detachable from the graspable surface 2s. In another embodiment, the kit comprises a plurality of contact surfaces 3, each of which is differently angled with respect to the longitudinal axis of the grasping element 25. In still another embodiment, the gene delivery device 1 comprises a housing defining a lumen 13 and having an opening in proximity with the contact surface 3, the lumen for delivering the pharmaceutical composition 16 to a tissue site 4 being contacted by the contact surface 3. In a further embodiment, the contact surface 3 is detachable from the housing. In still a further embodiment, the device 1 comprises a lumen 13 which in turn comprises a first 13a and second channel 13b. The first and second channels share a common wall 13w. In one embodiment of the invention, the kit comprises a selection of different shaft 2 housings.

The use of the device according to the present invention can also be facilitated by providing instructions with the kit. In one embodiment of the invention, the kit comprises instructions comprising data regarding how to perform the steps of the method. In another embodiment of the invention, the instructions are provided on a CD-ROM or video, or the like.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

EXAMPLE

Example 1

In one embodiment, carotid arteries from dogs were obtained for ex vivo transduction with a pharmaceutical composition (or "transduction solution") containing AdLacZ, an adenoviral vector expressing recombinant β-galactosidase gene. Carotid arteries were sectioned into 1.5–2 cm rings and five groups of treated rings were compared: (1) a negative control group receiving no virus; (2) a virus control group receiving AdeNOS (an adenoviral vector expressing recombinant eNOS gene); (3) a group receiving AdLacZ by immersion into a solution of AdLacZ or by dripping AdLacZ over the ring (e.g., via pipette); (4) a group receiving AdLacZ applied with the gene delivery device 1; and (5) a group receiving AdLacZ mixed with fibrin glue and applied with the gene delivery device 1.

As shown in Table 1, a number of parameters were tested using the gene delivery device. The titer of virus applied ranged from 10 to $1.5 \times 10^9$ PFU/ring (i.e., $10^7$, $10^8$, $10^9$, and $1.5 \times 10^9$ PFU/ring). While staining with BluoGal (a blue chromogenic substrate for β-galactosidase; Gibco BRL) was observed at $10^9$ PFU in groups not contacted with the contacting surface 3 of the gene delivery device 1, superior staining was observed even at vector concentrations 100-fold lower (i.e., as low as $10^7$ PFU) in tissue sites 4 contacted with the contact surface 3 of the gene delivery device 1.

TABLE 1

Paintbrush-Assisted Gene Delivery Technique
In Canine Carotid Artery*

| Parameter | Variation | Maximum** |
|---|---|---|
| Vector Titer Per Ring | $10^7$–$1.5 \times 10^9$ PFU/ring | $10^9$ PFU/ring |
| Transduction Volume | 20–150 μL/ring | 20 μL/cm² |
| Transduction Solution | DMEM, PBS | PBS |
| Transduction Time | 5–45 minutes | 10 minutes |
| Paintbrush Bristle | Fine, coarse | Coarse |
| Number Of Brush Strokes | 2–12 strokes/ring | 12 strokes/ring |
| Stroke Pressure | Ultralight, light, heavy | Light |

*Using AdlacZ vector; n = 7 dogs.
**Maximum staining using BluoGal histochemistry (i.e., defined as entirely blue artery)

Optimal transduction volumes (i.e., the amount of solution comprising the pharmaceutical composition 16) were also measured and compared with efficiency of gene delivery. Transduction volumes of 20, 40, 80, 100, 150, and 200 μL (microliters) of transduction solution were compared. In tissue sites 4 contacted with the gene delivery device 1, 20 μL/cm² of tissue site 4 was optimal while in tissue sites 4 not exposed to the device 1, 150 μL/cm² was optimal. Compared with conventional transduction methods, use of the gene delivery device 1 was found to be beneficial in greatly reducing (by over 7-fold) the volume of transduction solution required for effective transduction.

Transduction time (i.e., the time of direct exposure of the tissue site 4 to the transduction solution) was also examined across a range from 5 to 60 minutes. Maximum gene transfer was observed at 10 minutes using the gene delivery device, compared with 30–60 minutes without it. Compared with conventional transduction methods, use of the gene delivery device 1 was found to be beneficial in greatly reducing (by approximately 6-fold) the time required for effective transduction.

The stiffness of contact elements 3e on the contact surface was also varied. For example, the effect on transduction using fine bristles (made from camel hair) compared with coarse bristles (made from horse hair) was also studied. Compared with fine bristles, the use of coarse bristles was associated with up to 4-fold greater gene transfer efficacy.

The number of brush strokes per ring required to achieve maximal gene transfer was determined testing 2, 4, 6, and 12 strokes per ring (applying 20 μL, or 4 drops, of pharmaceutical composition per stroke). Twelve strokes per ring was observed to produce optimal BluoGal staining, while exposure to the same volume of solution without using the device 1 resulted in at least 10-fold less BluoGal staining. Brush stroking was not associated with any impairment of vascular structure or function as determined histologically (comparing cross-sections of brushed versus non-brushed rings in the presence and absence of virus) and via isometric force recording (comparing the vasoreactivity of brushed versus non-brushed rings in the presence and absence of virus, to endothelium-dependent and -independent vasoactive agents such as bradykinin and potassium chloride).

Stroke pressure, defined as the amount of compression of the ring upon contact with the contact surface 3, was varied. Ultralight pressure produced no deformation of the ring. Light pressure produced mild deformation (i.e., <15% change in the diameter of the ring). Heavy pressure produced extensive deformation of the ring (>>15% change in diameter), i.e., the ring was almost flattened. Light pressure by the contact surface 3 was associated with maximal transduction. Compared with conventional transduction (no-contact) methods, light pressure by the contact surface 3 resulted in a greater than 10-fold increase in gene transfer efficacy as measured by BluoGal staining. On the other hand, heavy pressure greatly reduced gene transfer efficacy to near-zero.

In one embodiment, the effect of the presence or absence of fibrin glue on gene transfer efficacy was determined. Fibrinogen (F; a polymerizable compound) to thrombin (T; a polymerizing agent) ratios of (F:T=) 1:1, 2:1, 5:1, 10:1, 25:1, and 50:1 were tested. A F:T ratio of 1:1 was found to be optimal with regard to rapidity of glue-setting (i.e., time to turn from a liquid to a semi-solid form, i.e., to effectively polymerize). At a 1:1 ratio, the glue had a relatively rapid set-time of 5 seconds. Virus was mixed with fibrinogen and contacted with the tissue site 4 prior to exposure to thrombin. The presence of the glue caused no tissue cytotoxicity as observed histologically. Further, as measured biochemically, although the efficiency of vector transduction using the glue applied by the contact surface 3 of device 1 was approximately 4- to 5-fold greater compared with conventional methods (FIG. 8A), the glue did result in less (i.e., almost halving) gene transfer efficiency compared to vector applied by the contact surface 3 of device 1 in the absence of fibrin glue (FIG. 8B). This correlated with morphologic findings (FIGS. 7A and 7B), where the presence of fibrin glue as applied by device 1 was associated with a linear localization of the vector along the tissue site 4, rather than a more diffuse (circumferential) staining pattern observed when the vector was applied with device 1 in the absence of fibrin glue.

Thus, use of the gene delivery device 1 increased both the efficacy and localization of gene transfer. These results are summarized in FIGS. 5A–5F, which are qualitative graphs. The Y-axis scale represents a minimum at zero and a maximum at the top of the scale (i.e., the point at which maximal staining with BluoGal is observed), providing a comparison of the relative increases or decreases in gene transfer efficacy during variation of different parameters.

Figure 6C:
Figure 6B:
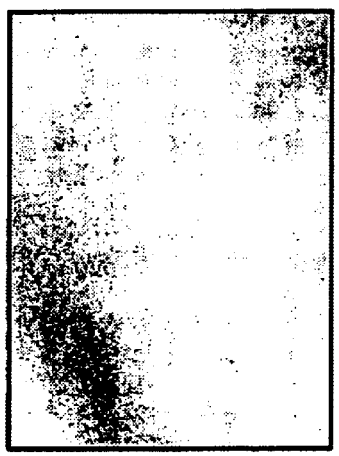
Figure 6A:
Figure 6E:
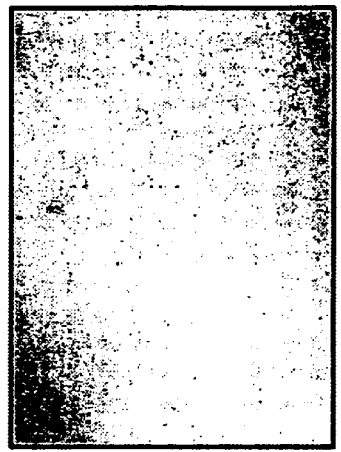
Figure 6D:

FIGS. 6A–6E show the effects of using the gene delivery device 1 on the expression of β-galactosidase, measured by BluoGal straining. FIG. 6A shows no detectable BluoGal staining in a ring brushed with a solution comprising no nucleic acids. FIG. 6B shows minimal β-galactosidase expression when the ring is immersed in a solution comprising $10^9$ PFU of AdLacZ. FIG. 6C shows enhanced, more diffuse staining after immersing the ring in a solution comprising $10^9$ AdLacZ precipitated with 6 mmol/L calcium phosphate ($CaP_i$)—this precipitation technique is reputed to be the most effective means available of increasing recombinant virus-mediated gene transfer efficacy (Morling, et al., Gene Therapy 2: 504–508, 1995; Toyoda, et al., Gene Therapy 7: 1284–1291, 2000). FIG. 6D shows considerably greater enhancement of BluoGal staining when AdLacZ is brushed by gene delivery device 1 in the presence of fibrin glue (FG). Even greater enhancements are observed using AdLacZ brushed by gene delivery device 1 in the absence of FG (not shown). Straining is maximal at tissue sites 4 contacted with the contact surface 3 of the gene delivery device 1. FIG. 6E shows that no staining is observed after contacting an adenoviral vector not expressing β-galactosidase, but expressing AdeNOS instead, with the contact surface 3. In brief, FIGS. 6A–6E demonstrate that application of an adenoviral vector using gene delivery device 1 results in transduction considerably over and above that observed by conventional immersion, with or without $CaP_i$ precipitation. In the examples shown in FIGS. 6A, 6D and 6E, the contact surface 3 was the bristles of a paintbrush; the bristles were horse hair, and 12 strokes were used with a light stroke pressure. The fibrinogen:thrombin ratio was 1:1 in FIG. 6D. The transduction volume was 20 μL/$cm^2$ for brushed rings, and 150 μL for immersed rings. The transduction time was 10 minutes.

Figure 7B:
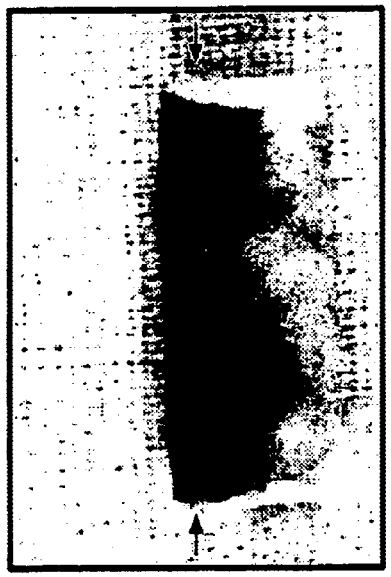
FIGS. 7A and 7B shows the effect of using a gene delivery device according to one embodiment of the invention, with and without fibrin glue, on expression of a marker gene encoding β-galactosidase.
Figure 7A:
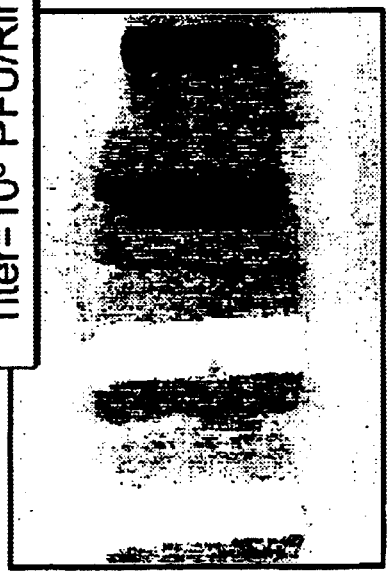

FIGS. 7A and 7B show the effect of contacting a tissue site 4 (in this case the adventitia or outer wall of an artery) with a contact surface 3 of a gene delivery device 1 according to the invention. In this embodiment, $10^9$ PFU of virus was used per arterial ring. As can be seen in FIG. 7A, a greater than 10-fold increase in BluoGal staining was observed when applying AdLacZ using the gene delivery device 1 (see ZB and ZFGB) compared with contact by immersion (ZD). The negative control ring (NCB), which was brushed using device 1 with virus-free medium, shows no BluoGal staining as expected. The presence of fibrin glue (ZFGB) during light-brushing of AdLacZ into the arterial wall with device 1 did result in enhanced localization of staining compared to light-brushing of AdLacZ in the absence of fibrin glue (ZB; compare with ZFGB), however the absolute amount of staining was less in the presence of fibrin glue (FIG. 7B) than in its absence using the device 1.

Figure 8A:
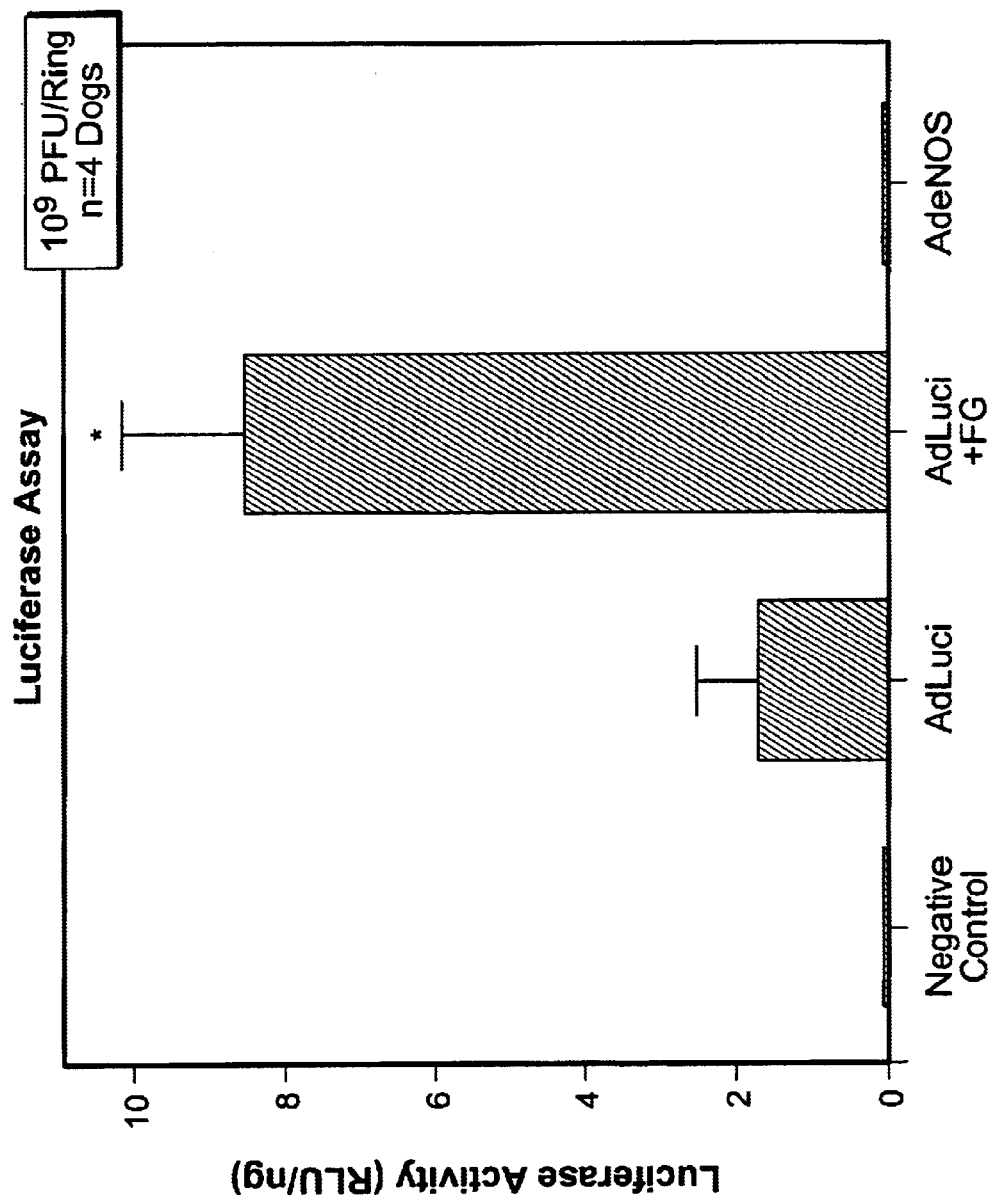
FIG. 8 shows the effect of using a gene delivery device on the expression of a marker gene encoding luciferase (FIG. 8A) or β-galactosidase (FIG. 8B).
Figure 8B:
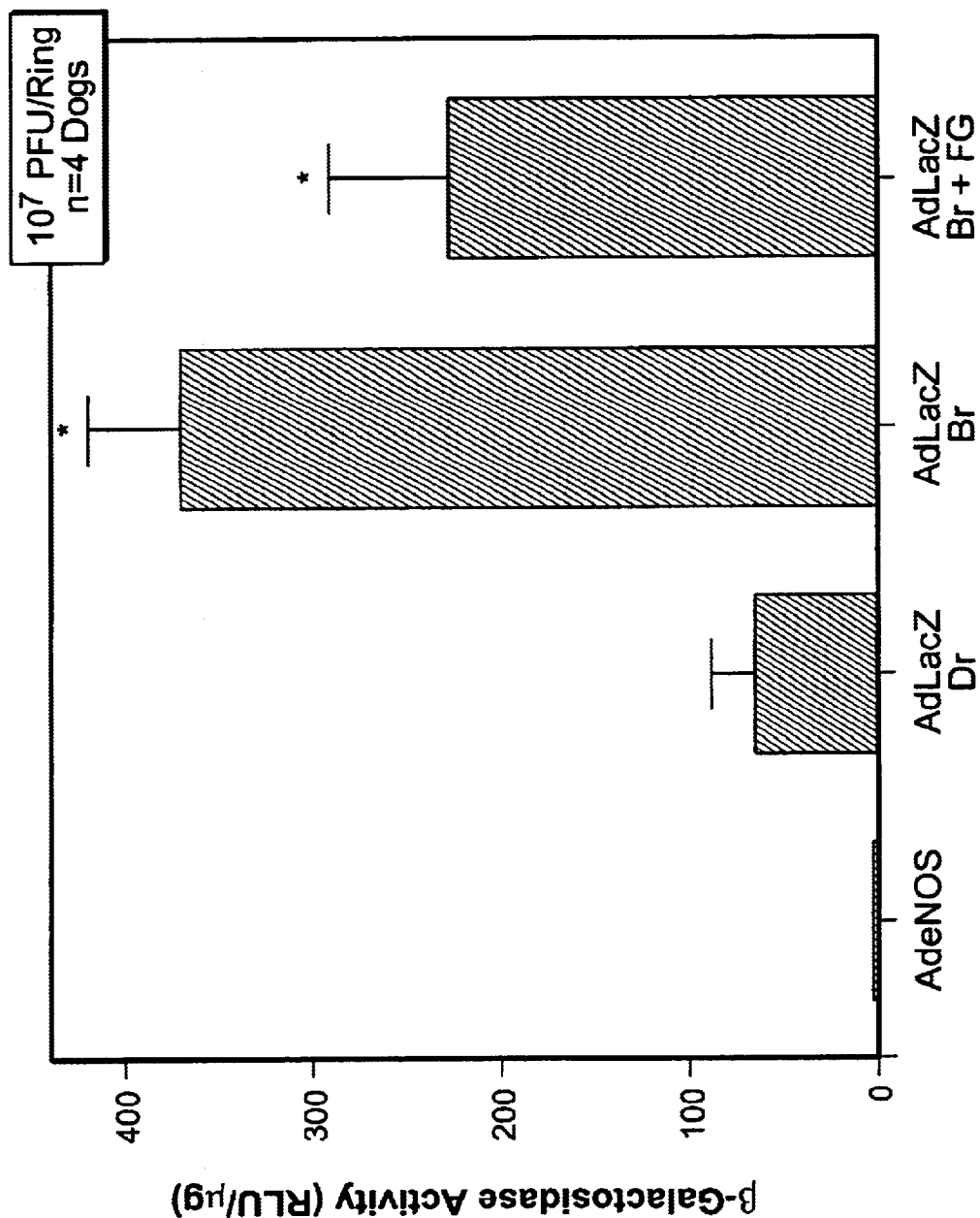

FIGS. 8A and 8B show the effect of application of a vector using gene delivery device 1 compared with conventional methods, as measured biochemically via the expression of a recombinant gene product, namely, luciferase (FIG. 8A) or μ-galactosidase (FIG. 8B). In FIG. 8A, note the 4- to- 5-fold increase in transduction of AdLuci (adenovirus expressing recombinant luciferase gene) in canine middle cerebral artery rings brushed using device 1 in the presence of fibrin glue (AdLuci+FG) compared with rings immersed in vector (AdLuci) alone. The vector concentration used is $10^9$ PFU/ring, and the data are from 4 dogs. The Y-axis represents the amount of luciferase enzyme activity measured, depicted in relative light units per nanogram of protein (RLU/ng). The device-brushed ring exposed to virus-free media (negative control) and the device-brushed ring exposed to a control, non-luciferase virus (AdeNOS) had no measurable luciferase activity, as expected. In FIG. 8B, note the 5- to 6-fold increase in transduction of AdLacZ in canine carotid artery rings brushed using device 1 in the absence of fibrin glue (AdLacZ Br) compared with rings immersed in vector (AdLacZ Dr) alone. For this data set, the vector concentration used is $10^7$ PFU/ring, and the data are from another 4 dogs. The Y-axis represents the amount of β-galactosidase enzyme activity measured, depicted in relative light units per microgram of protein (RLU/μg). The device-brushed ring exposed to a control, non-AdLacZ virus (AdeNOS) had no measurable β-galactosidase activity above minor background levels, as expected. Together, these biochemical data confirm the morphologic data, indicating that, compared to conventional methods, there is a significantly large enhancement in recombinant gene expression following delivery of a vector using the device 1-mediated brushing technique described in this invention.

FIG. 9 depicts key biological considerations for an optimal gene therapy paradigm. These considerations include: (1) a disease of known molecular pathogenesis, with supportive animal and human tissue experimental models; (2) an informed, consenting patient whose condition and treatment meets the rigorous criteria defined by government and institutional regulatory bodies; (3) a clinically safe vector comprised of a suitable biological agent (such as a minimal-genome adenovirus), a therapeutic gene of interest, and a regulatory element to control gene expression; (4) a delivery instrument (e.g., an effective brush-based device as described in this invention) and appropriate mode of delivery (i.e., ex vivo versus in vivo; intraoperative versus nonoperative; intraluminal versus periadventitial approach); (5) efficient and tissue-specific transduction; and (6) a therapeutic benefit which must be objectively and clinically measurable.

Example 2

In this embodiment, the gene delivery device 1 is used to optimize gene delivery parameters in different human tissues. Human tissues obtained from "surgical waste" (e.g., biopsies or other surgical procedures) are tested morphologically, biochemically, or functionally, after contact with the gene delivery device 1 and a pharmaceutical composition 16 or after exposure to the pharmaceutical composition 16 by immersion. Tissue samples obtained include, but are not limited to, brain parenchyma and vascular tissue from temporal lobectomy procedures, or from cerebrovascular or tumor surgery; vascular and/or atherosclerotic tissue from carotid or peripheral vascular endarterectomy/revascularization procedures, tissue from lung, bowel, or bone resections, endocrine tissue from thyroidectomy, pancreatectomy, adrenalectomy, and/or tissues from consenting human donors.

Example 3

In one embodiment, the gene delivery device 1 is used in an in vivo rabbit experimental model. Experimental groups: There are 4 major groups (n=6 rabbits each, referred to as groups A–D) and 2 minor groups (n=2 rabbits each, referred to as groups E and F). The 12 rabbits in groups A and C receive a conventional (high) dose of adenovirus expressing recombinant β-galactosidase (AdLacZ). The 12 rabbits in groups B and D receive a low dose of AdLacZ. In each AdLacZ group, the adenovirus vector is a component of pharmaceutical composition 16. The 4 rabbits in groups E and F will receive no adenovirus (i.e., negative controls). Group A and B rabbits have high and low doses, respectively, of adenovirus gently brushed using device 1 at specific tissue sites 4 (see surgical procedures below) on their left side using a pure-bristle paintbrush, and a high dose of adenovirus dripped onto corresponding tissue sites 4 on their right side using a sterile pipette tip. Group C and D rabbits have high and low doses, respectively, of adenovirus gently brushed using device 1 at other specific tissue sites (see surgical procedures below) on their left side using a pure-bristle paintbrush, and a low dose of adenovirus dripped onto corresponding tissue sites on their right side using a sterile pipette tip. Group E rabbits undergo the same procedure as group A and B rabbits, except using saline only, brushed in by device 1 on the left side, and dripped on the right side. Group F rabbits undergo the same procedure as group C and D rabbits, except using saline only, brushed in by device 1 on the left side, and dripped on the right side (i.e., Group E and F rabbits are sham-operated, negative controls).

Doses of vector: High-dose refers to the conventional adenoviral titer of $1.5 \times 10^9$ PFU per target tissue site 4. Low-dose refers to a titer of $10^7$ PFU per target tissue site 4, and is based on our canine ex vivo optimization data (Table 1; FIGS. 5–8) using the paintbrush method. This low dose is 150 times lower than the conventional (high) titer, and has been shown to be effective in the aforementioned ex vivo experiments.

Tissue Sites: The effects of paintbrushing versus conventional dripping of virus are studied at the following five tissue sites (see surgical procedure section, below): (1) left and right carotid artery, (2) left and right sternocleidomastoid muscle, and (3) left and right peritoneum in Group A, B, and E rabbits; and (4) left and right shaved upper-dorsal intact skin, and (5) left and right shaved lower-dorsal incised/sutured skin in Group C, D, and F rabbits. Group E and F rabbits are not be exposed to virus, only saline.

The efficacy and specificity of paintbrush-mediated gene delivery versus conventional dripping method is determined by comparing the amount of AdLacZ staining (via BluoGal histochemistry) in "brushed" versus "dripped" carotid artery segments. These arterial segments are stained and examined macroscopically and histologically for extent and distribution of staining. Histologic examination also allow determination of any major disruption of tissue architecture that may have occurred, particularly with the brushing method (the aforementioned ex vivo data suggest that light arterial brushing is not associated with any tissue injury whatsoever).

Assessment of vasomotor function is evaluated by comparing the vasomotor reactivity (via isometric force recording) in "brushed" versus "dripped" carotid artery segments, to those of known historical controls. Relaxations and contractions are performed to common vasoactive substances such as acetylcholine, bradykinin, phenylepherine, endothelin-1, and potassium chloride. Concentration-response curves are generated using routine methods so that agonist efficacy and potency in both of these treatment groups can be compared with published historical controls. These findings will provide additional important information with regard to the paintbrush method's effect on vasomotor integrity. The ex vivo data to date suggest there is no vasomotor impairment associated with light brushing of arteries using device 1 as described in this invention. Non-vascular sites being amenable to paintbrush-assisted gene delivery are identified by determining the efficacy of brushing on non-vascular tissue sites such as the sternocleidomastoid muscle, shaved skin, skin incision/wound, and peritoneum. These tissues are stained ex vivo using BluoGal histochemical method, and comparisons are made between "brushed" versus "dripped" tissues.

The time-frame of the investigation is generally 48 hours (Day 0–2), based on ex vivo findings of optimal recombinant β-galactosidase gene expression at this time point. Rabbits are fed the normal Purina chow diet. Peripheral blood samples drawn from the ear artery will be collected on Day 0 (day of surgery) and Day 2 (day of sacrifice) in order to assess, via white-cell count, the degree of leukocytosis as a marker for any degree of inflammation following exposure to virus. Rabbits are closely assessed clinically for signs of distress, withdrawal, or sepsis.

Example 4

In one embodiment, a patient is anesthetized, positioned, aseptically prepared and draped according to standard neurosurgical practice. A skin incision is made and intracranial access gained either by minimal access surgery (e.g., keyhole surgery) or open craniotomy, as appropriate. A target blood vessel(s) is visualized. Once opening dissection is complete and hemostasis secured by cautery, a clinical-grade vector incorporating a therapeutic gene of interest is contacted using light pressure with a gene delivery device 1 (e.g., a paint brush) manipulated by the surgeon.

The surgeon physically transfers the pharmaceutical composition 16 to the tissue site 4 using 2–12 brush strokes/cm² of tissue. In one embodiment, a biosafe-biocompatible dye incorporated in the pharmaceutical composition 16 is used to allow the surgeon to visualize the region of delivery/application. The pharmaceutical composition 16 is allowed to dry on the blood vessel for a minimum of 10 minutes in an otherwise dry operative field (e.g., cleared by suction prior to application of the vector). Hemostasis is confirmed visually and the opening is closed in layers as per standard practice. In one embodiment, the gene delivery device 1, is mounted using a suitable medical access device such as an endoscopic adapter device inserted through a keyhole opening in the skin. Visualization in this embodiment is performed using a camera or "scope" inserted locoregionally through a separate keyhole in physical proximity to the keyhole through which the medical access device is inserted.

The expression of a marker gene and/or the therapeutic gene is determined either by measuring the presence of the gene(s) in a circulating body fluid (in the case of the marker gene) or obtaining a small tissue sample for molecular analyses (e.g., antibody staining or RT-PCR). Vasomotor function is also monitored angiographically or ultrasonographically, and the specificity of the procedure is monitored by confirming the expression of the therapeutic gene at the tissue site 4 (e.g., the blood vessel wall) and the absence of the therapeutic gene's expression at a tissue site not contacted with the gene delivery device.

The pharmaceutical composition in one embodiment comprises less than $1.5 \times 10^9$ PFU of an adenoviral vector expressing a therapeutic gene. In a further embodiment of the invention, antibiotics, antipyretic, and/or intravenous fluids are provided, either using the gene delivery device 1 or by some other route of administration, as appropriate.

Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

What is claimed is:

1. A method for delivering a pharmaceutical composition comprising a nucleic acid to a tissue site of an animal or human, comprising the steps of:
   providing a graspable gene delivery device comprising a contact surface;
   applying said pharmaceutical composition to said contact surface; and
   contacting said contact surface to said tissue site, wherein said contacting is by moving said contact surface across said tissue site,
   wherein said gene delivery device comprises a lumen defining an opening such that fluid exiting said opening comes in contact with said contact surface, and wherein said applying comprises delivering said pharmaceutical composition through said opening to said contact surface.

2. A method for delivering a pharmaceutical composition comprising a nucleic acid to a tissue site of an animal or human, comprising the steps of:
   providing a graspable gene delivery device comprising a contact surface;
   applying said pharmaceutical composition to said contact surface; and
   contacting said contact surface to said tissue site, wherein said contacting is by moving said contact surface across said tissue site,
   wherein said pharmaceutical composition further comprises a polymerizable agent, which polymerizes when said contact surface is contacted to said tissue site.

3. The method according to claim 1, wherein said lumen comprises a first and second channel sharing a common wall, and said method further comprises delivering a polymerizable compound through said first channel and a polymerizing agent through said second channel, and wherein said polymerizing agent is polymerized by said polymerizing agent at said tissue site.

4. A method according to claim 3, wherein said pharmaceutical composition is mixed with said polymerizable compound.

5. A kit, comprising:
   a gene delivery device comprising a contact surface for contacting a tissue, wherein said contact surface comprises bristles; and
   a pharmaceutical composition comprising a nucleic acid, a polymerizeable compound, and a polymerizing agent.

6. A kit, comprising:
   a gene delivery device comprising a graspable surface for attachment to a contact surface;
   at least one contact surface for attachment to said graspable surface, wherein said contact surface comprises bristles; and;
   a pharmaceutical composition comprising a dye or other detectable moiety, a polymerizeable compound, a polymerizing agent, and a nucleic acid.

7. The kit according to claim 5 or 6, wherein said nucleic acid is DNA.

8. The kit according to claim 5 or 6, wherein said nucleic acid is RNA, an anti-sense molecule, a triple-helix-forming nucleic acid, an aptamer, or a ribozyme.

9. The kit according to claim 5 or 6, wherein said polymerizeable compound is fibrinogen and said polymerizing agent is thrombin.

10. The kit according to claim 5 or 6, wherein said gene delivery device comprises a graspable surface having a longitudinal axis, and said contact surface is detachable from said graspable element.

11. The kit according to claim 6, wherein said contact surface comprises a plurality of contact surfaces, each of which are differently angulated with respect to the longitudinal axis of the graspable surface.

12. The kit according to claim 5 or 6, wherein said gene delivery device further comprises a housing defining a lumen and having an opening such that fluid exiting said opening comes in contact with said contact surface, said lumen for delivering said pharmaceutical composition to a tissue site being contacted by the contact surface.

13. The kit according to claim 12, further comprising a double-barreled syringe and conduit-tubing.

14. A device for delivering a pharmaceutical composition to a tissue, comprising:
   a housing having a first end and a second end and defining a lumen, said first end comprising an opening;
   a contact surface for contacting a tissue, wherein said contact surface comprises a plurality of bristles at least partially surrounding said opening, wherein said contact surface is detachably connected to said first end of said housing, and
   wherein said contact surface is connected to said housing via an adapter.

15. A device for delivering a pharmaceutical composition to a tissue, comprising:
   a housing having a first end and a second end and defining a lumen, said first end
   a contact surface for contacting a tissue, wherein said contact surface comprises a plurality of bristles at least partially surrounding said opening, wherein said contact surface is detachably connected to said first end of said housing, and
   wherein said contact surface is adjustable to an angle that is 0–180° angle with respect to the longitudinal axis of the housing.

16. A device for delivering a pharmaceutical composition to a tissue, comprising:
   a housing having a first end and a second end and defining a lumen, said first end comprising an opening;
   a contact surface for contacting a tissue, wherein said contact surface comprises a plurality of bristles at least partially surrounding said opening, wherein said contact surface is detachably connected to said first end of said housing, and
   wherein said lumen further comprises a first and second channel, said first and second channel sharing a common wall.

17. A device for delivering a pharmaceutical composition to a tissue, comprising:
   a housing having a first end and a second end and defining a lumen, said first end comprising an opening;
   a contact surface for contacting a tissue, wherein said contact surface comprises a plurality of bristles at least partially surrounding said opening, wherein said contact surface is detachably connected to said first end of said housing, and wherein said second end of said housing is connectable to a syringe or conduit-tubing.

18. The device of claim 17, wherein said syringe and conduit tubing are double-barreled.

19. A device for delivering a pharmaceutical composition to a tissue, comprising:

a housing having a first end and a second end and defining a lumen, said first end comprising an opening;

a contact surface for contacting a tissue, wherein said contact surface comprises a plurality of bristles at least partially surrounding said opening, wherein said contact surface is detachably connected to said first end of said housing, and wherein said first end comprises a plurality of openings.

20. A kit comprising a device for delivering a pharmaceutical composition to a tissue, and a pharmaceutical composition comprising a nucleic acid, wherein said device comprises:

a housing having a first end and a second end and defining a lumen, said first end comprising an opening;

a contact surface for contacting a tissue, wherein said contact surface comprises a plurality of bristles at least partially surrounding said opening, and wherein said contact surface is connected to said first end of said housing.

21. A device for delivering a pharmaceutical composition to a tissue, comprising:

a housing having a first end and a second end and defining a lumen, said first end comprising an opening;

a contact surface for contacting a tissue, wherein said contact surface comprises a plurality of bristles at least partially surrounding said opening, wherein said contact surface is connected to said first end of said housing, wherein said contact surface is adjustable to an angle that is 0–180° with respect to the longitudinal axis of said housing, and wherein said lumen further comprises a first and second channel, said first and second channel sharing a common wall.

22. A device for delivering a pharmaceutical composition to a tissue, comprising:

a housing having a first end and a second end and defining a lumen, said first end comprising an opening;

a contact surface for contacting a tissue, wherein said contact surface comprises a plurality of bristles at least partially surrounding said opening, wherein said contact surface is connected to said first end of said housing, wherein said contact surface is adjustable to an angle that is 0–180° with respect to the longitudinal axis of said housing, and wherein said first end comprises a plurality of openings.

23. The kit according to claim 20, wherein said nucleic acid is DNA.

24. The kit according to claim 20, wherein said nucleic acid is RNA, an anti-sense molecule, a triple-helix-forming nucleic acid, an aptamer, or a ribozyme.

25. The kit according to claim 20, wherein said contact surface is detachable from said housing.

26. The kit according to claim 20, wherein said device comprises a plurality of contact surfaces, each of which are differently angulated with respect to the longitudinal axis of said housing.

* * * * *